US009012727B2

(12) United States Patent
Chatani et al.

(10) Patent No.: US 9,012,727 B2
(45) Date of Patent: Apr. 21, 2015

(54) GENES THAT INCREASE PLANT OIL AND METHOD FOR USING THE SAME

(71) Applicant: Toyota Jidosha Kabushiki Kaisha, Toyota-shi, Aichi-ken (JP)

(72) Inventors: Hiroshi Chatani, Okazaki (JP); Chikara Ohto, Toyota (JP); Yukio Okamura, Nagoya (JP); Norihiro Mitsukawa, Miyoshi (JP); Nobuhiko Muramoto, Ichinomiya (JP); Masaru Takagi, Tsuchiura (JP); Nobutaka Mitsuda, Tsukuba (JP); Tomotsugu Koyama, Tsukuba (JP); Kyoko Matsui, Ryugasaki (JP)

(73) Assignee: Toyota Jidosha Kabushiki Kaisha, Aichi-ken (JP)

( * ) Notice: Subject to any disclaimer, the term of this patent is extended or adjusted under 35 U.S.C. 154(b) by 0 days.

(21) Appl. No.: 14/280,163

(22) Filed: May 16, 2014

(65) Prior Publication Data

US 2014/0303352 A1    Oct. 9, 2014

Related U.S. Application Data

(62) Division of application No. 12/746,577, filed as application No. PCT/JP2008/072159 on Dec. 5, 2008, now Pat. No. 8,847,011.

(30) Foreign Application Priority Data

Dec. 5, 2007 (JP) .................................. 2007-315267

(51) Int. Cl.
| | | |
|---|---|---|
| C12N 15/82 | (2006.01) | |
| C12P 21/02 | (2006.01) | |
| C12N 15/09 | (2006.01) | |
| C07H 21/04 | (2006.01) | |
| A01H 1/00 | (2006.01) | |
| A01H 5/10 | (2006.01) | |
| C07K 7/06 | (2006.01) | |
| C07K 14/415 | (2006.01) | |

(52) U.S. Cl.
CPC .............. *C12N 15/8247* (2013.01); *C07K 7/06* (2013.01); *C07K 14/415* (2013.01); *C12N 15/8216* (2013.01); *C12N 15/8217* (2013.01); *C12N 15/8261* (2013.01); *C12N 15/8245* (2013.01)
USPC ....... 800/295; 800/281; 435/320.1; 435/69.1; 435/69.7; 536/23.4; 536/23.6

(58) Field of Classification Search
None
See application file for complete search history.

(56) References Cited

U.S. PATENT DOCUMENTS

| | | |
|---|---|---|
| 5,516,668 A | 5/1996 | Maruta |
| 5,783,394 A | 7/1998 | Bestwick et al. |
| 5,914,449 A | 6/1999 | Murase et al. |
| 6,717,034 B2 | 4/2004 | Jiang |
| 7,342,148 B2 | 3/2008 | Takagi et al. |
| 2003/0101481 A1 | 5/2003 | Zhang et al. |
| 2003/0226173 A1 | 12/2003 | Ratcliffe et al. |
| 2004/0006797 A1 | 1/2004 | Shi et al. |
| 2004/0045049 A1 | 3/2004 | Zhang et al. |
| 2004/0093638 A1 | 5/2004 | Sasaki et al. |
| 2005/0005333 A1 | 1/2005 | Ruezinsky et al. |
| 2005/0183169 A1 | 8/2005 | Takagi et al. |
| 2006/0107345 A1 | 5/2006 | Alexandrov et al. |
| 2006/0272060 A1 | 11/2006 | Heard et al. |
| 2007/0022495 A1 | 1/2007 | Reuber et al. |
| 2008/0072340 A1 | 3/2008 | Troukhan et al. |
| 2008/0096277 A1 | 4/2008 | Kuroda |
| 2009/0019605 A1 | 1/2009 | Takagi et al. |
| 2009/0094717 A1 | 4/2009 | Troukhan et al. |
| 2009/0116723 A1 | 5/2009 | Okajima et al. |
| 2009/0178161 A1 | 7/2009 | Arar et al. |
| 2009/0190821 A1 | 7/2009 | Marugame |
| 2009/0300790 A1 | 12/2009 | Aharoni et al. |
| 2010/0311994 A1 | 12/2010 | Chatani et al. |
| 2011/0081691 A1 | 4/2011 | Ohto et al. |
| 2011/0099664 A1 | 4/2011 | Takagi et al. |
| 2011/0209244 A1 | 8/2011 | Takagi et al. |

(Continued)

FOREIGN PATENT DOCUMENTS

| | | |
|---|---|---|
| EP | 1 469 010 A1 | 10/2004 |
| EP | 1586652 A1 | 10/2005 |

(Continued)

OTHER PUBLICATIONS

Alex Cernac et al., "WRINKLED1 encodes an AP2/EREB domain protein involved in the control of storage compound biosynthesis in *Arabidopsis*", The Plant Journal, 2004, pp. 575-585, vol. 40, Blackwell Publishing Ltd.
Anders M. Lindroth et al., "Requirement of CHROMOMETHYLASE3 for Maintenance of CpXpG Methylation", Science, Jun. 2001, pp. 2077-2080, vol. 292, American Association for the Advancement of Science, Washington, DC.

(Continued)

*Primary Examiner* — Eileen B O Hara
*Assistant Examiner* — Matthew Keogh
(74) *Attorney, Agent, or Firm* — Sughrue Mion, PLLC

(57) ABSTRACT

This invention is intended to be used to search for a transcription factor having novel functions of increasing the weight of an individual plant, increasing the weight of a given tissue per individual plant, or improving the productivity of a given substance per individual plant and to improve such properties in the plant. The weight of an individual plant is increased, the weight of a given tissue per individual plant is increased, the productivity of a given substance per individual plant is improved, or the content of a given substance per given tissue of a plant is increased via expression of a transcription factor that has been modified to suppress transcription accelerating activity.

10 Claims, 4 Drawing Sheets

(56) References Cited

U.S. PATENT DOCUMENTS

| | | |
|---|---|---|
| 2012/0144522 A1 | 6/2012 | Kondo et al. |
| 2012/0159666 A1 | 6/2012 | Yonekura et al. |
| 2012/0159673 A1 | 6/2012 | Kondo et al. |

FOREIGN PATENT DOCUMENTS

| | | |
|---|---|---|
| EP | 1702508 A1 | 9/2006 |
| JP | 60-2023 B2 | 1/1985 |
| JP | 02-035358 A | 2/1990 |
| JP | 06-090766 A | 4/1994 |
| JP | 6-217719 A | 8/1994 |
| JP | 6-303925 A | 11/1994 |
| JP | 9-182 A | 1/1997 |
| JP | 9-65840 A | 3/1997 |
| JP | 9-313059 A | 12/1997 |
| JP | 2001-059842 A | 3/2001 |
| JP | 3149951 B2 | 3/2001 |
| JP | 2001-269176 A | 10/2001 |
| JP | 2001-269177 A | 10/2001 |
| JP | 2001-269178 A | 10/2001 |
| JP | 2001-269179 A | 10/2001 |
| JP | 2001-292776 A | 10/2001 |
| JP | 2001-292777 A | 10/2001 |
| JP | 2001-333705 A | 12/2001 |
| JP | 3289043 B2 | 6/2002 |
| JP | 2002-524028 A | 8/2002 |
| JP | 3407033 B2 | 3/2003 |
| JP | 3407034 B2 | 3/2003 |
| JP | 3407035 B2 | 3/2003 |
| JP | 3407036 B2 | 3/2003 |
| JP | 3409079 B2 | 3/2003 |
| JP | 3421740 B2 | 4/2003 |
| JP | 2004-500823 A | 1/2004 |
| JP | 2004-286666 A | 10/2004 |
| JP | 2005-013214 A | 1/2005 |
| JP | 2005-27654 A | 2/2005 |
| JP | 2005-052114 A | 3/2005 |
| JP | 3656104 B2 | 3/2005 |
| JP | 2005192483 A | 7/2005 |
| JP | 2005-204573 A | 8/2005 |
| JP | 2005-204657 A | 8/2005 |
| JP | 2005-278422 A | 10/2005 |
| JP | 2005-295878 A | 10/2005 |
| JP | 2005-295879 A | 10/2005 |
| JP | 2005-325136 A | 11/2005 |
| JP | 2005-352571 A | 12/2005 |
| JP | 2006-6248 A | 1/2006 |
| JP | 2006-20607 A | 1/2006 |
| JP | 2006-34218 A | 2/2006 |
| JP | 2006-42729 A | 2/2006 |
| JP | 2006-42730 A | 2/2006 |
| JP | 2006-55125 A | 3/2006 |
| JP | 2006-101827 A | 4/2006 |
| JP | 2006-134188 A | 5/2006 |
| JP | 2006-325588 A | 7/2006 |
| JP | 3829200 B2 | 7/2006 |
| JP | 2006-280242 A | 10/2006 |
| JP | 3995211 B2 | 10/2007 |
| JP | 2008-502358 A | 1/2008 |
| JP | 2009-009290 A | 1/2009 |
| JP | 2009-115598 A | 5/2009 |
| JP | 2009-180539 A | 8/2009 |
| JP | 2009-210409 A | 9/2009 |
| WO | 00/05385 A1 | 2/2000 |
| WO | 01/35727 A1 | 5/2001 |
| WO | 01/36597 A1 | 5/2001 |
| WO | 01/64022 A2 | 9/2001 |
| WO | 03/013227 A2 | 2/2003 |
| WO | 03/055903 A1 | 7/2003 |
| WO | 2004/031349 A2 | 4/2004 |
| WO | 2004/046336 A2 | 6/2004 |
| WO | 2004/056993 A1 | 7/2004 |
| WO | 2005047516 A2 | 5/2005 |
| WO | 2005/085467 A1 | 9/2005 |
| WO | 2006/056701 A1 | 6/2006 |
| WO | 2006133461 A1 | 12/2006 |
| WO | 2007/102346 A1 | 9/2007 |
| WO | 2007/117693 A2 | 10/2007 |
| WO | 2008/041693 A1 | 4/2008 |
| WO | 2010/035618 A1 | 4/2010 |
| WO | 2010/041423 A1 | 4/2010 |

OTHER PUBLICATIONS

Colette Jako et al., "Seed-Specific Over-Expression of an *Arabidopsis* cDNA Encoding a Diacylglycerol Acyltransferase Enhances Seed Oil Content and Seed Weight", Plant Physiology, Jun. 2001, pp. 861-874, vol. 126, American Society of Plant Physiologists.

Daniel Zilberman et al., "ARGONAUTE4 Control of Locus-Specific siRNA Accumulation and DNA and Histone Methylation", Science, Jan. 2003, pp. 716-719, vol. 299, American Association for the Advancement of Science.

J. Christopher Gaiser et al., "The *Arabidopsis* SUPERMAN Gene Mediates Asymmetric Growth of the Outer Integument of Ovules", The Plant Cell, Mar. 1995, pp. 333-345, vol. 7, American Society of Plant Physiologists.

James P. Jackson et al., "Control of CpNpG DNA methylation by the KRYPTONITE histone H3 methyltransferase", Letter to Nature, Apr. 2002, pp. 556-560, vol. 416, Macmillan Magazines Ltd.

John L. Bowman et al., "SUPERMAN, a regulator of floral homeotic genes in *Arabidopsis*", Development, 1992, pp. 599-615, vol. 114, The Company of Biologists Limited, Great Britian.

Keiichiro Hiratsu et al., "Dominant repression of target genes by chimeric repressors that include the EAR motif, a repression domain, in *Arabidopsis*", The Plant Journal, 2003, pp. 733-739, vol. 34, Blackwell Publishing Ltd.

Keiichiro Hiratsu et al., "Identification of the minimal repression domain of SUPERMAN shows that the DLELRL hexapeptide is both necessary and sufficient for repression of transcription in *Arabidopsis*", Biochemical and Biophysical Research Communications, 2004, pp. 172-178, vol. 321, Elsevier Inc.

Keiichiro Hiratsu et al., "The SUPERMAN protein is an active repressor whose carboxy-terminal repression domain is required for the development of normal flowers", Federation of European Biochemical Societies, 2002, pp. 351-354, vol. 514, Elsevier Science B.V.

Keith Roesler et al., "Targeting of the *Arabidopsis* Homomeric Acetyl-Coenzyme A Carboxylase to Plastids of Rapeseeds", Plant Physiology, 1997, pp. 75-81, vol. 113, Clearance Center.

Koji Goto et al., "Function and regulation of the *Arabidopsis* floral homeotic gene *pistillata*", Genes & Development, 1994, pp. 1548-1560, vol. 8, Cold Spring Harbor Laboratory Press.

Kyoko Matsui et al., "Suppression of the biosynthesis of proanthocyanidin in *Arabidopsis* by a chimeric PAP1 repressor", Plant biotechnology Journal, 2004, pp. 487-493, vol. 2, Blackwell Publishing Ltd.

Kyoko Matsui, "A Chimeric AtMYB23 Repressor Induces Hairy Roots, Elongation of Leaves and Stems, and Inhibition of the Deposition of Mucilage on Seed Coats in *Arabidopsis*", Plant Cell Physiology, 2005, pp. 147-155, vol. 46(1).

Kyoko Matsui et al., "Bio Medical Quick Review Net", 2004, pp. 1-6, vol. 4006.

Lu Tian et al., "Blocking histone deacetylation in *Arabidopsis* induces pleiotropic effects on plant gene regulation and development", PNAS, Jan. 2001, pp. 200-205, vol. 98, No. 1.

Masaru Ohta et al., "Repression Domains of Class II ERF Transcriptional Repressors Share and Essential Motif for Active Repression", The Plant Cell, Aug. 2001, pp. 1959-1968, vol. 13, American Society of Plant Biologists.

Steven E. Jacobsen et al., "Ectopic hypermethylation of flower-specific genes in *Arabidopsis*", Current Biology, 2000, pp. 179-186, vol. 10, Elsevier Science Ltd.

Steven E. Jacobsen et al., "Hypermethylated SUPERMAN Epigenetic Alleles in *Arabidopsis*", Science, 1997, pp. 1100-1103, vol. 277, American Association for the Advancement of Science, Washington, DC.

(56) References Cited

OTHER PUBLICATIONS

Xiaofeng Cao et al., "Locus-specific control of asymmetric and CpNpG methylation by to DRM and CMT3 methyltransferase genes", Colloguium, PNAS, Dec. 2002, pp. 16491-16498, vol. 99.

Xiaofeng Cao et al., "Role of the *Arabidopsis* DRM Methyltransferases in De Novo DNA Methylation and Gene Silencing", Current Biology, Jul. 2002, pp. 1138-1144, vol. 12, Elsevier Science Ltd.

Nobutaka Mitsuda et al., "Comprehensive functional analysis of plant-specific NAC transcription factor family using the CRES-T method", Abstracts of the 45th Annual Meeting of the Japanese Society of Plant Physiologists, Mar. 2004, P4-B-16 (813).

S. Takada et al., GenBank Accession AB049071, GI:12060425, 2006, 3 pages.

K. Yamada et al., GenBank Accession BT005044, GI:28827465, 2003, 2 pages.

Extended European Search Report (EESR) for corresponding European Patent Application No. 08 85 6425 dated Nov. 3, 2010.

V.R. Bautista et al., "*Arabidopsis* ORF clones", GenBank Accession BT029518, 2006, retrieved from: http://www.ncbi.nlm.nih.gov/entrez/viewer.fcgi?119360090:NCBI:15965543 on Dec. 25, 2008.

Mingjie Chen et al., "System Analysis of an *Arabidopsis* Mutant Altered in de Novo Fatty Acid Synthesis Reveals Diverse Changes in Seed Composition and Metabolism", Plant Physiology, 2009, 150: 27-41.

Antony N. Dodd et al., "Plant Circadian Clocks Increase Photosynthesis, Growth, Survival, and Competitive Advantage", Science, 2005, 309: 630-633.

John Doebley et al., "The evolution of apical dominance in maize", Nature, 1997, 386: 485-488.

Christian Dubos et al., "MYB transcription factors in *Arabidopsis*", Trends in Plant Science, 2010, 15(10): 573-581.

Extended European Search Report for corresponding European Patent Application No. 08858128.5 dated Nov. 15, 2010.

Haiwei H. Guo et al., "Protein tolerance to random amino acid change", PNAS, 2004, 101(25): 9205-9210.

Yongfeng Guo et al., "AtNAP, a NAC family transcription factor, has an important role in leaf senescence", The Plant Journal, 2006, 46: 601-612.

Yuxin Hu et al., "The *Arabidopsis* Auxin-Inducible Gene ARGOS Controls Lateral Organ Size", The Plant Cell, 2003, 15: 1951-1961.

Yuxin Hu. et al., "The *Arabidopsis* ARGOS-LIKE gene regulates cell expansion during organ growth", The Plant Journal, 2006, 47:1-9.

International Search Report for International Application No. PCT/JP2008/072158, dated Feb. 24, 2009.

International Search Report for International Application No. PCT/JP2010/059543, dated Aug. 17, 2010.

Tomotsugu Koyama et al., "TCP Transcription Factors Control the Morphology of Shoot Lateral Organs via Negative Regulation of the Expression of Boundary-Specific Genes in *Arabidopsis*", The Plant Cell, 2007, 19: 473-484.

Minoru Kubo et al., "Transcription switches for protoxylem and metaxylem vessel formation", Genes & Development, 2005, 19: 1855-1860.

Norihito Kuno et al., "The Novel MYB Protein Early-Phytochrome-Responsive1 Is a Component of a Slave Circadian Oscillator in *Arabidopsis*", The Plant Cell, 2003, 15: 2476-2488.

Makoto Kusaba et al., "Low glutelin content1: A Dominant Mutation that Suppresses the Glutelin Multigene Family via RNA Silencing in Rice", The Plant Cell, 2003, 15: 1455-1467.

Hon-Ming Lam, et al., "Overexpression of the ASN1 Gene Enhances Nitrogen Status in Seeds of *Arabidopsis*", Plant Physiology, 2003, 132: 926-935.

Jisheng Li et al., "*Arabidopsis* H+-PPase AVP1 Regulates Auxin-Mediated Organ Development", Science, 2005, 310: 121-125.

Yoshiyuki Maruta et al., "Transgenic rice with reduced glutelin content by transformation with glutelin A antisense gene", Molecular Breeding, 2001, 8:273-284.

Kyoko Matsui et al., "AtMYBL2, a protein with a single MYB domain, acts as a negative regulator of anthocyanin biosynthesis in *Arabidopsis*", The Plant Journal, 2008, 55: 954-967.

Akane Matsushita et al., "AGF1, an AT-Hook Protein, Is Necessary for the Negative Feedback of AtGA3ox1 Encoding GA 3-Oxidase", Plant Physiology, 2007, 143: 1152-1162.

Nobutaka Mitsuda et al., "NAC Transcription Factors, NST1 and NST3, Are Key Regulators of the Formation of Secondary Walls in Woody Tissues of *Arabidopsis*", The Plant Cell, 2007, 19: 270-280.

Yukiko Mizukami et al., "Plant organ size control: AINTEGUMENTA regulates growth and cell numbers during organogenesis", PNAS, 2000, 97(2): 942-947.

Nobuhiko Muramoto et al., "Identification of transcription factors responsible for seed oil content by Chimeric Repressor Gene-Silencing Technology (CRES-T)", Suppplemental to Plant and Cell Physiology, 2008, 49: 152.

Toshitsugu Nakano et al., "Genome-Wide Analysis of the ERF Gene Family in *Arabidopsis* and Rice", Plant Physiology, 2006, 140: 411-432.

Zhongfu Ni et al., "Altered circadian rhythms regulate growth vigour in hybrids and allopolyploids", Nature, 2009, 457: 327-331.

Akio Ohyama et al., "Environmental risk evaluation of rice plants transformed with chimeric antisense cDNA for glutelin", Breeding Research, 2001, 3: 139-149.

Y. Pan et al., "Molecular Cloning, Expression, Phylogenetic and Functional Characterization of the *Arabidopsis* AP2/EREBP Transcription Factor Family", Gen Bank Accession AY560877, 2004 retrieved from: http://www.ncbi.nlm.nih.gov/entrez/viewer.fcgi?48479345:NCBI:6713742 on Dec. 25, 2008.

"Represent" from Merriam-Webster Dictionary, Retrieved from http://www.merriam-webster.com/dictionary/represents on Feb. 5, 2013.

Diego Mauricio Riaño-Pachón et al., "Pln TFDB an intergrative plant transcription factor database", BMC Bioinformatics, 2007, 8(42): 1-10.

Monica Santos-Mendoza et al., "Deciphering gene regulatory networks that control seed development and maturation in *Arabidopsis*", The Plant Journal, 2008, 54: 608-620.

Shinichrio Sawa et al., "Overexpression of the AtmybL2 Gene Represses Trichome Development in *Arabidopsis*", DNA Research, 2002, 9: 31-34.

Marie C. Schruff et al., "The Auxin Response Factor 2 gene of *Arabidopsis* links auxin signalling, cell division, and the size of seeds and other organs", Development, 2005 133: 251-261.

Bo Shen et al., "The homeobox gene GLABRA2 affects seed oil content in *Arabidopsis*", Plant Molecular Biology, 2006, 60: 377-387.

Ralf Stracke et al., "The R2R3-MYB gene family in *Arabidopsis thaliana*", Current Opinion in Plant Biology, 2001, 4: 447-456.

Taito Takeda et al., "RNA interference of the *Arabidopsis* putative transcription factor TCP16 gene results in abortion of early pollen development", Plant Molecular Biology, 2006, 61: 165-177.

Geoffrey M. Wahl et al., "Molecular Hybridization of Immobilized Nucleic Acids: Theoretical Concepts and Practical Considerations", Methods in Enzymology, 1987, 152: 399-407.

Randall J. Weselake et al., "Increasing the flow of carbon into seed oil", Biotechnology Advances, 2009, 27: 866-878.

Joseph A. White et al., "Genomic approaches towards the engineering of oil seeds", Plant Physiology and Biochemistry, 2001, 39: 263-270.

Chen Yanhui et al., "The MYB transcription factor superfamily of *Arabidopsis*: expression analysis and phylogenetic comparison with the rice MYB family", Plant Molecular Biology, 2006, 60(1): 107-124.

James Z. Zhang, "Overexpression Analysis of Plant Transcription Factors", Current Opinion in Plant Biology, 2003, 6: 430-440.

Election of Species Requirement issued Aug. 16, 2012 in U.S. Appl. No. 12/746,640.

Non-final Office Action issued Nov. 27, 2012 in U.S. Appl. No. 12/746,640.

Final Office Action issued Jul. 2, 2013 in U.S. Appl. No. 12/746,640.

Non-final Office Action issued Feb. 19, 2013 in U.S. Appl. No. 12/921,060.

(56) References Cited

OTHER PUBLICATIONS

Final Office Action issued in U.S. Appl. No. 12/921,060, dated Oct. 8, 2013.
Summaries of a Conference of Japan Society for Bioscience, Biotechnology and Agrochemistry, 2008, p. 64.
Accession No. NM_102146, *Arabidopsis thaliana* AP2 domain-containing transcription factor, putative (AT1G22985) mRNA, complete cds, Database (online), May 2009, retrieved from http://www.ncbi.nlm.nih.gov/nuccore/30688157?sat=13&satkey=2426001 on Feb. 6, 2014.
Zhang et al., Journal of Experimental Botany, 2008, 59(15):4095-4107.
Ohto, 22$^{nd}$ International Conference on *Arabidopsis* Research, 2011, Publication: 501746623.
Jofuku et al., PNAS, 2005, 102(8):3117-3122.
Office Action, issued by the United States Patent and Trademark Office on Jan. 2, 2015, in U.S. Appl. No. 13/376,169.
Notice of Allowance, issued by the United States Patent and Trademark Office on Feb. 11, 2015, in U.S. Appl. No. 12/921,060.
Office Action, issued by the United States Patent and Trademark Office on Feb. 11, 2015, in U.S. Appl. No. 13/376,138.
Office Action, issued by the United States Patent and Trademark Office on Feb. 13, 2015, in U.S. Appl. No. 13/376,326.
Notice of Allowance, issued by the United States Patent and Trademark Office on Feb. 11, 2015, in U.S. Appl. No. 14/222,130.

GENES THAT INCREASE PLANT OIL AND METHOD FOR USING THE SAME

CROSS REFERENCE TO RELATED APPLICATIONS

This application is a Divisional of U.S. patent application Ser. No. 12/746,577, filed Sep. 8, 2010, which is a National Stage of International Application No. PCT/JP2008/072159 filed Dec. 5, 2008, claiming priority based on Japanese Patent Application No. 2007-315267, filed Dec. 5, 2007, the contents of all of which are incorporated herein by reference in their entirety.

BACKGROUND ART

The term "biomass" generally refers to the total amount of organisms that inhabit or exist in a given area. When such term is used for plants, in particular, the term refers to dry weight per unit area. A biomass unit is quantified in terms of a mass or an energy amount. In the case of plant biomass, the term "standing crop" is occasionally used to represent "biomass." Since plant biomass is generated by fixing atmospheric carbon dioxide with the use of the solar energy, it can be regarded as so-called "carbon-neutral energy." Accordingly, an increase of plant biomass is effective for global environmental preservation, the prevention of global warming, and mitigation of greenhouse gas emissions. Thus, technologies for increasing the production of plant biomass have been industrially significant.

Plants are cultivated for the purpose of using some tissues thereof (e.g., seeds, roots, leaves, or stems) or for the purpose of producing various materials, such as a fat and oil. Examples of fat and oil produced from plants that have been heretofore known include soybean oil, sesame oil, olive oil, coconut oil, rice oil, cottonseed oil, sunflower oil, corn oil, safflower oil, and rapeseed oil. Such fat and oil are extensively used for household and industrial applications. Also, a fat and oil produced from plants is used as biodiesel fuels, and the applicability thereof is increasing for alternative energy to petroleum.

Under such circumstances, it is necessary for the industrial success of the production of the fat and oil using plants that the productivity per unit of cultivation area be improved. If the number of cultivated plants is assumed to be constant per unit of cultivation area, an improvement in the amount of fat and oil production per plant is found to be necessary. When fat and oil are extracted from seeds obtained from plants, an improvement in the amount of fat and oil production per plant can be achieved via techniques of, for example, improving the seed yield per plant or increasing the fat and oil content in seeds.

Techniques for increasing the amount of fat and oil production from plant seeds are roughly classified into techniques based on an improvement in cultivation methods and techniques based on the development of plant varieties that can increase the amount of fat and oil production. Techniques based on the development of plant varieties are roughly classified as conventional breeding techniques such as crossing and molecular breeding techniques via genetic recombination. As techniques for increasing the amount of fat and oil production via genetic recombination, A) a method of modifying synthetic pathways for triacylglycerol (TAG) of seeds, which is a main component of plant fat and oil, and B) a method of modifying regulatory genes that regulate plant morphogenesis or metabolism are known.

In the method A) above, the amount of TAGs synthesized from sugars produced via photosynthesis can be increased by (1) enhancing synthesis activities of a fatty acids (i.e., TAG components) or a glycerol from sugars or (2) reinforcing the reaction of synthesizing TAGs from glycerol and fatty acids. In this regard, the following techniques have been reported as techniques using genetically engineering techniques. An example of (1) is a technique in which cytosolic Acetyl-coenzyme A carboxylase (ACCase) of *Arabidopsis thaliana* is overexpressed in plastids of *Brassica rapa* L. ver. Nippo-oleifera and the fat and oil content in seeds is improved by 5% (Plant Physiology, 1997, Vol. 113, pp. 75-81).

An example of (2) is a technique of increasing the fat and oil production via overexpression of diacylglycerol acyltransferase (DGAT) that transfers an acyl group to the sn-3 position of diacylglycerol (Plant Physiology, 2001, Vol. 126, pp. 861-874). It is reported that the fat and oil content and the seed weight are increased as the DGAT expression level increases, and the number of seeds per plant may be occasionally increased according to the method of Plant Physiology, 2001, Vol. 126, pp. 861-874. The fat and oil content in *Arabidopsis thaliana* seeds was increased by 46% and the fat and oil amount per plant was increased by a maximum of about 125% by such technique.

As the method of B), expression of transcriptional factor genes associated with regulation of biosynthetic enzyme genes expression may be regulated. An example thereof is WO 01/35727. WO 01/35727 employs a technique in which recombinant plants are prepared via exhaustive overexpression or knocking out of transcriptional factors and genes that enhance the fat and oil content in seeds are then selected. WO 01/35727 discloses that overexpression of ERF subfamily B-4 transcriptional factor genes results in a 23% increase in the fat and oil content in seeds. WO 01/35727, however, does not disclose an increase or decrease in fat and oil content per plant. Also, Plant J., 2004, 40, 575-585 discloses the overexpression of WRINKLED1, which is a transcriptional factor having the AP2/EREB domain, improves the fat and oil content in seeds.

Although molecular breeding techniques as described above intended for the improvement of various traits have been developed, techniques for improving the yield involving increasing the weight of plant, increasing a given tissue, or improving the productivity of target substances have not yet been put to practical use.

Further, targets of techniques for increasing the production of target substances (fat and oil, in particular) via genetic recombination are dicotyledonous plants such as *Arabidopsis thaliana* and *Brassica rapa* L. ver. Nippo-oleifera. Techniques targeting monocotyledonous plants, such as rice and maize, are not yet known.

This is considered to be due to the following reasons. That is, truly excellent genes have not yet been discovered and new recombinant varieties that are found effective at the test phase cannot exhibit effects as expected during the practical phase under a variety of natural environments. In order to overcome such problems, the discovery of dramatically effective new genes and the development of genes exhibiting effects under practical environments, even if the effectiveness thereof is equivalent to that of existing genes, are necessary.

DISCLOSURE OF THE INVENTION

Object to be Attained by the Invention

Under given circumstances, the present invention is intended to be used to search for a transcription factor having new functions of increasing the weight of an individual plant, increasing the weight of a given tissue per individual plant, improving the productivity of a given substance per individual plant, or increasing the content of a given substance in a given tissue of a plant and to provide a technique that is capable of improving such features in a plant.

Means for Attaining the Object

The present inventors have conducted concentrated studies in order to attain the above object. As a result, they discovered that expression of a transcription factor that is modified so as to suppress transcription accelerating activity would lead to an increase in the weight of an individual plant, an increase in the weight of a given tissue per individual plant, an improvement in the productivity of a given substance per individual plant, or an increase in the content of a given substance in a given tissue of a plant. This has led to the completion of the present invention.

The plant according to the present invention attained increased individual plant weight, increased weight of a given tissue per individual plant, improved productivity of a given substance per individual plant, or increased content of a given substance in a given tissue of a plant via expression of a transcription factor with suppressed transcription accelerating activity.

In the present invention, transcription factor that belongs to the transcription factor family including a transcription factor comprising the amino acid sequence as shown in SEQ ID NO: 2, a transcription factor comprising the amino acid sequence as shown in SEQ ID NO: 4, a transcription factor comprising the amino acid sequence as shown in SEQ ID NO: 6, a transcription factor comprising the amino acid sequence as shown in SEQ ID NO: 8, a transcription factor comprising the amino acid sequence as shown in SEQ ID NO: 10, a transcription factor comprising the amino acid sequence as shown in SEQ ID NO: 12, and a transcription factor comprising the amino acid sequence as shown in SEQ ID NO: 14 can be used as the above-mentioned transcription factor.

The transcription factor is preferably any of proteins (a) to (c) below:

(a) a protein comprising the amino acid sequence as shown in SEQ ID NO: 2, 4, 6, 8, 10, 12, or 14;

(b) a protein comprising an amino acid sequence derived from the amino acid sequence as shown in SEQ ID NO: 2, 4, 6, 8, 10, 12, or 14 by deletion, substitution, addition, or insertion of 1 or a plurality of amino acids and having transcription accelerating activity; or (c) a protein encoded by a polynucleotide hybridizing under stringent conditions to a polynucleotide comprising a nucleotide sequence complementary to the nucleotide sequence as shown in SEQ ID NO: 1, 3, 5, 7, 9, 11, or 13 and having transcription accelerating activity.

In particular, the plant according to the present invention can have suppressed transcription accelerating activity of a target transcription factor by expressing a chimeric protein resulting from the fusion of the target transcription factor with a functional peptide that converts an arbitrary transcription factor into a transcription repressor in a plant. Examples of the functional peptides include peptides represented by formulae (1) to (8) below:

$$X1\text{-Leu-Asp-Leu-}X2\text{-Leu-}X3 \tag{1}$$

wherein X1 represents 0 to 10 amino acid residues; X2 represents Asn or Glu; and X3 represents at least 6 amino acid residues;

$$Y1\text{-Phe-Asp-Leu-Asn-}Y2\text{-}Y3 \tag{2}$$

wherein Y1 represents 0 to 10 amino acid residues; Y2 represents Phe or Ile; and Y3 represents at least 6 amino acid residues;

$$Z1\text{-Asp-Leu-}Z2\text{-Leu-Arg-Leu-}Z3 \tag{3}$$

wherein Z1 represents Leu, Asp-Leu, or Leu-Asp-Leu; Z2 represents Glu, Gln, or Asp; and Z3 represents 0 to 10 amino acid residues;

$$\text{Asp-Leu-}Z4\text{-Leu-Arg-Leu} \tag{4}$$

wherein Z4 represents Glu, Gln, or Asp;

$$\alpha 1\text{-Leu-}\beta 1\text{-Leu-}\gamma 1\text{-Leu;} \tag{5}$$

$$\alpha 1\text{-Leu-}\beta 1\text{-Leu-}\gamma 2\text{-Leu;} \tag{6}$$

$$\alpha 1\text{-Leu-}\beta 2\text{-Leu-Arg-Leu; and} \tag{7}$$

$$\alpha 2\text{-Leu-}\beta 1\text{-Leu-Arg-Leu;} \tag{8}$$

wherein, in formulae (5) to (8), $\alpha 1$ represents Asp, Asn, Glu, Gln, Thr, or Ser; $\alpha 2$ represents Asn, Glu, Gln, Thr, or Ser; $\beta 1$ represents Asp, Gln, Asn, Arg, Glu, Thr, Ser, or His; $\beta 2$ represents Asn, Arg, Thr, Ser, or His; $\gamma 1$ represents Arg, Gln, Asn, Thr, Ser, His, Lys, or Asp; and $\gamma 2$ represents Gln, Asn, Thr, Ser, His, Lys, or Asp.

In the plant according to the present invention, the seed weight as the weight of a given tissue can be improved. Also, in the plant according to the present invention, the productivity of a fat and oil as the productivity of a given substance described above can be improved.

The present invention can provide a method for producing a plant exhibiting increased individual plant weight, increased weight of a given tissue per individual plant, improved productivity of a given substance per individual plant, or increased content of a given substance in a given tissue of a plant via expression of a transcription factor with suppressed transcription accelerating activity.

Further, the present invention can provide a chimeric protein resulting from the fusion of a target transcription factor with a functional peptide that converts an arbitrary transcription factor into a transcription repressor, which is capable of increasing the weight of an individual plant, increasing the weight of a given tissue per individual plant, improving the productivity of a given substance per individual plant, or increasing the content of a given substance in a given tissue of a plant via suppression of transcription accelerating activity of the transcription factor; a polynucleotide encoding the chimeric protein; a recombinant expression vector containing the polynucleotide and a promoter; and a kit for improving properties of a plant in terms of the weight of a plant, the weight of a given tissue, the productivity of a given substance, or the content of a substance comprising the expression vector.

Effects of the Invention

The plant according to the present invention exhibits increased individual plant weight, increased weight of a given tissue per individual plant, improved productivity of a given substance per individual plant, or increased content of a given substance in a given tissue of a plant, compared with a wild-type plant. With the use of the plant according to the present invention, accordingly, the amount of production of the target biomass can be increased, the yield of the target tissue can be increased, the productivity of the target substance can be improved, and the content of the target substance in the target tissue can be increased. This enables production of biomass, plant tissue, or target substances at low cost.

Also, the chimeric protein according to the present invention can impart a plant with traits such as increased individual plant weight, increased weight of a given tissue per individual plant, improved productivity of a given substance per individual plant, or increased content of a given substance in a given tissue of a plant, compared with a wild-type plant. With the use of the chimeric protein according to the present invention, accordingly, a plant that can realize an increased amount of biomass production, increased yield of the target tissue, improved productivity of a target substance, or increased content of a target substance in the target tissue can be produced.

This description includes part or all of the contents as disclosed in the description and/or drawings of Japanese Patent Application No. 2007-315267, which is a priority document of the present application.

BEST MODES FOR CARRYING OUT THE INVENTION

Figure 1:
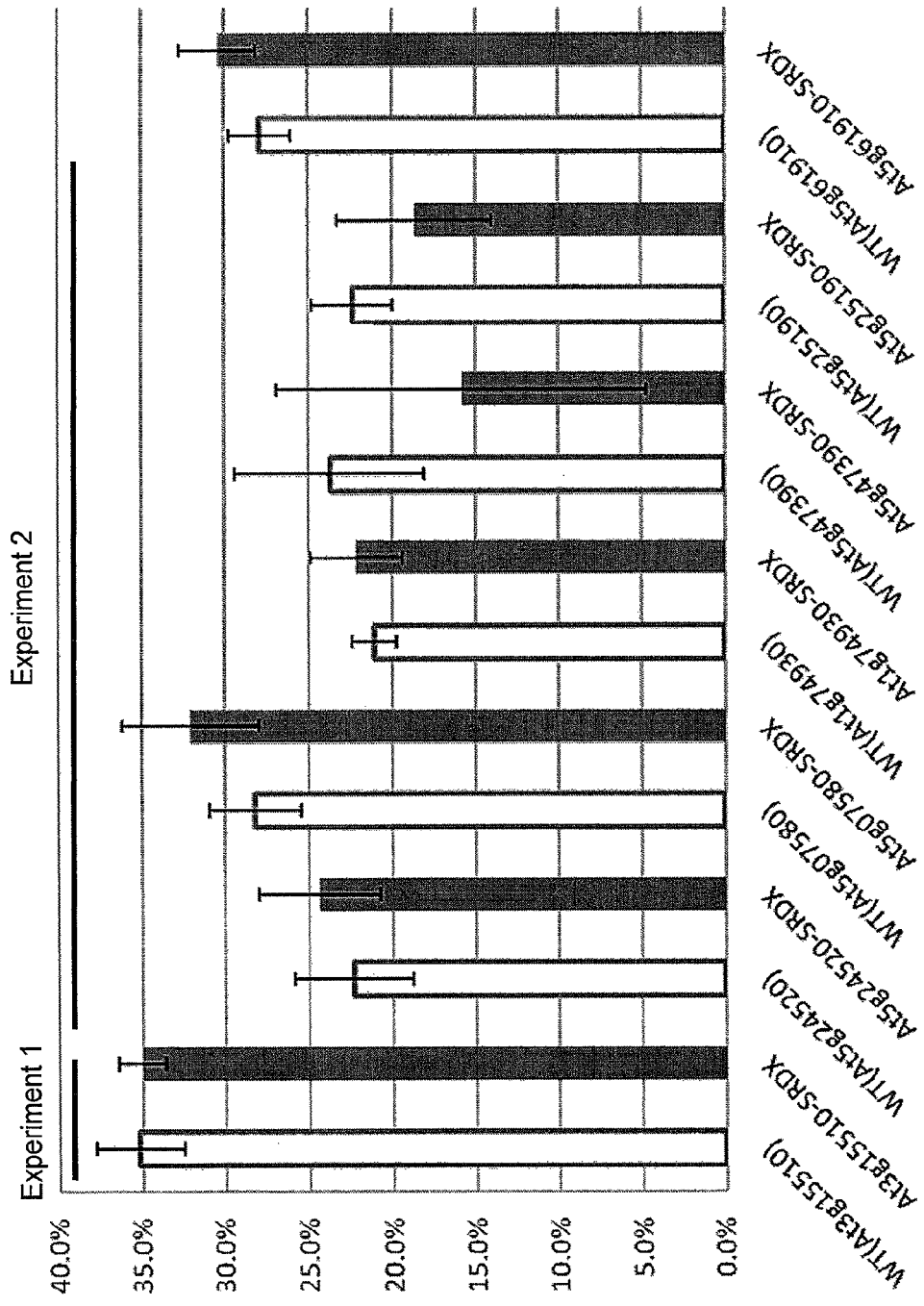
FIG. 1 is a characteristic diagram showing the results of measuring fat and oil contents in seeds of plants prepared in the examples (T2 plant-T3 seeds).

Hereafter, the present invention is described in detail.

The plant according to the present invention exhibits increased individual plant weight, increased weight of a given tissue per individual plant, improved productivity of a given substance per individual plant, or increased content of a given substance in a given tissue, compared with a wild-type plant, via expression of a transcription factor with suppressed transcription accelerating activity. Specifically, the plant according to the present invention was produced by expressing a transcription factor with suppressed transcription accelerating activity in a plant of interest, so as to significantly improve the weight of a plant, the weight of a given tissue, the productivity of a given substance, or the content of a given substance therein.

The term "the increased weight of a plant" used herein refers to an increase in production of so-called biomass, i.e., an increase in the amount of biomass per given area. The amount of biomass produced per given area can be increased by increasing the planting density (i.e., the number of individual plants per given area) and by increasing the weight or energy amount per individual plant. Specifically, plant biomass can be evaluated in terms of dry weight per individual plant, as well as in terms of dry weight per given area.

In the present invention, accordingly, biomass may be defined in terms of the plant dry weight per individual plant, the dry weight of aerial parts per individual plant, the weight of a given tissue accumulating the target product per individual plant, the target product per individual plant, or the content of the target substance per given tissue.

The term "the weight of a given tissue per individual plant" used herein refers to the weight of at least 1 tissue selected from among tissues such as seeds, roots, leaves, stems, flowers, and pollen that constitute plants. Particularly preferably, the plant according to the present invention is intended to increase seed weight.

The term "the productivity of a given substance per individual plant" used herein refers to the contents of various substances generated by plants per individual plant. Substances are not particularly limited and may be naturally produced by plants. Alternatively, such substances may be not naturally produced by plants, but rather may be produced from plants via genetic engineering or other means. If the content of the target product per tissue is increased, in particular, purification and transportation costs can be reduced, and the industrial usefulness of such plants is significant. Specifically, target products may be lignocelluloses that account for substantially the entire weight of a plant, plant fat and oil that is used as seed oils at the industrial level may be preferably used, and plant oils are particularly preferable. Plant oils may be simple lipids that is the esters of fatty acids with alcohols, complex lipid including phosphorus, sugar, nitrogen, and the like, or a fatty acid. An alcohol of a simple lipid may be a higher alcohol having a high molecular weight or a polyhydric alcohol, such as glycerol (glycerin). A fatty acid of a simple lipid may be a saturated fatty acid, unsaturated fatty acid, or special fatty acid comprising a hydroxyl group or an epoxy group. Simple lipids that are the esters of glycerol and fatty acid may be monoacylglycerol, diacylglycerol, or triacylglycerol.

Hereafter, substances that improve productivity are described with reference to a fat and oil, although the technical scope of the present invention is not limited thereto. The present invention is also applicable to substances other than the fat and oil as substances generated from plants.

The present invention can cover any plants without particular limitation. Angiosperms are particularly preferable as plants, and either monocotyledonous or dicotyledonous plants may be covered. Plants that have been heretofore used for the production of the fat and oil are particularly preferable. Examples of intended plants include soybeans, sesame, olive oils, coconuts, rice, cottons, sunflowers, maize, safflowers, and rapeseeds. Also, *Arabidopsis thaliana*, which is extensively used as a model organism in genetic analysis of plants and for which a method for gene expression analysis has been established can be intended.

The term "transcription factor with suppressed transcription accelerating activity" refers to a transcription factor having transcription accelerating activity significantly lower than the activity that the transcription factor would naturally have. Methods for lowering transcription accelerating activity are not particularly limited. Gene-silencing techniques can be extensively employed, and a method of constructing a fusion protein to which a repressor domain sequence has been added is the most preferable.

In such a technique, "repressor domain sequences" are amino acid sequences constituting peptides that convert arbitrary transcription factors into transcription repressors, and the present inventors have discovered a wide variety of such sequences.

Techniques involving the use of repressor domain sequences are disclosed in, for example, JP Patent Publication (kokai) No. 2001-269177 A, JP Patent Publication (kokai) No. 2001-269178 A, JP Patent Publication (kokai) No. 2001-292776 A, JP Patent Publication (kokai) No. 2001-292777 A, JP Patent Publication (kokai) No. 2001-269176 A, JP Patent Publication (kokai) No. 2001-269179 A, WO 03/055903, Ohta, M., Matsui, K., Hiratsu, K., Shinshi, H. and Ohme-Takagi, M., The Plant Cell, Vol. 13, 1959-1968, August, 2001, and Hiratsu, K., Ohta, M., Matsui, K., Ohme-Takagi, M., FEBS Letters 514, 2002, 351-354. Repressor domain sequences are cleaved from Class II ethylene-responsive element binding factor (ERF) proteins or plant zinc finger proteins (e.g., the *Arabidopsis thaliana* SUPERMAN protein) and have very simple structures.

Examples of transcription factors with transcription accelerating activity to be suppressed include the transcription factor identified as At3g15510 in *Arabidopsis thaliana* (hereafter simply referred to as the "transcription factor At3g15510"), the transcription factor identified as At5g24520 in *Arabidopsis thaliana* (hereafter simply referred to as the "transcription factor At5g24520"), the transcription factor identified as At5g07580 in *Arabidopsis thaliana* (hereafter simply referred to as the "transcription factor At5g07580"), the transcription factor identified as At1g74930 in *Arabidopsis thaliana* (hereafter simply referred to as the "transcription factor At1g74930"), the transcription factor identified as At5g47390 in *Arabidopsis thaliana* (hereafter simply referred to as the "transcription factor At5g47390"), the transcription factor identified as At5g25190 in *Arabidopsis thaliana* (hereafter simply referred to as the "transcription factor At5g25190"), and the transcription factor identified as At3g61910 in *Arabidopsis thaliana* (hereafter simply referred to as the "transcription factor At3g61910").

There is no report regarding functions of the transcription factor At3g15510. The transcription factor At5g24520 is a transcription factor having the WD40 repeat, it is known as a TTG1 gene, and functions thereof that regulates the flavonoid/anthocyanin synthesis (Plant Cell, 2001 September; 13 (9): 2099-114, and Plant J. 2006 June; 46 (5): 768-79) or patterning of epidermal cells (e.g., trichome or root hair) (Curr Opin Plant Biol., 2003 February; 6 (1): 74-8) have been reported. The transcription factor At5g07580 is classified into the B-3 subfamily of the AP2/ERF family, and there is no report regarding functions thereof. The transcription factor At1g74930 is classified into the A-5 subfamily of the AP2/ERF family, and there is no report regarding functions thereof. The transcription factor At5g47390 is a transcription factor of the myb family protein, and there is no report regarding functions thereof. The transcription factor At5g25190 is a transcription factor of the AP2/ERF family, and there is no report regarding functions thereof. The transcription factor At3g61910 is an NAC transcription factor. The transcription factor At3g61910 is reported as a transcription factor that regulates secondary thickening of a cell wall (Plant Cell, 2005 November; 17 (11): 2993-3006). Also, it is reported that overexpression of genes of the transcription factor At3g61910 to which a repressor domain sequence had been added suppresses secondary thickening of a cell wall.

The amino acid sequences of such transcription factors and the nucleotide sequences of the coding regions of the genes encoding such transcription factors are summarized in Table 1.

TABLE 1

| Transcription factor | Amino acid sequence | Nucleotide Sequence |
| --- | --- | --- |
| At3g15510 | SEQ ID NO: 2 | SEQ ID NO: 1 |
| At5g24520 | SEQ ID NO: 4 | SEQ ID NO: 3 |
| At5g07580 | SEQ ID NO: 6 | SEQ ID NO: 5 |
| At1g74930 | SEQ ID NO: 8 | SEQ ID NO: 7 |
| At5g47390 | SEQ ID NO: 10 | SEQ ID NO: 9 |
| At5g25190 | SEQ ID NO: 12 | SEQ ID NO: 11 |
| At3g61910 | SEQ ID NO: 14 | SEQ ID NO: 13 |

The specific transcription factors with transcription accelerating activity to be suppressed are not limited to those comprising the amino acid sequences as shown in SEQ ID NOs: 2, 4, 6, 8, 10, 12, and 14. An intended transcription factor may be a transcription factor comprising an amino acid sequence derived from the amino acid sequence as shown in SEQ ID NO: 2, 4, 6, 8, 10, 12, or 14 by deletion, substitution, addition, or insertion of 1 or a plurality of amino acids and having transcription accelerating activity. The number of such plurality of amino acids is, for example, 1 to 20, preferably 1 to 10, more preferably 1 to 7, further preferably 1 to 5, and particularly preferably 1 to 3. Deletion, substitution, or addition of amino acids can be conducted by modifying a nucleotide sequence encoding the above-mentioned transcription factor via a method known in the art. Mutation can be introduced into a nucleotide sequence via known methods, such as the Kunkel or Gapped duplex method, or methods in accordance therewith. For example, mutation is introduced with the use of mutagenesis kits utilizing site-directed mutagenesis (e.g., Mutant-K or Mutant-G (tradenames, manufactured by TAKARA)) or the LA PCR in vitro Mutagenesis Series Kit (tradename, manufactured by TAKARA).

Further, transcription factors with transcription accelerating activity to be suppressed are not limited to transcription factors At3g15510, At5g24520, At5g07580, At1g74930, At5g47390, At5g25190, and At3g61910 in *Arabidopsis thaliana*, and transcription factors (hereafter referred to as "homologous transcription factors) having equivalent functions in plants other than *Arabidopsis thaliana* (e.g., plants mentioned above) are within the scope of the present invention. The homologous transcription factors corresponding to the transcription factors At3g15510, At5g24520, At5g07580, At1g74930, At5g47390, At5g25190, and At3g61910 can be searched for, in case that the plant genome information has been revealed, using the genome information of the intended plant based on the amino acid sequences of the transcription factors At3g15510, At5g24520, At5g07580, At1g74930, At5g47390, At5g25190, and At3g61910 or the nucleotide sequences of the genes encoding such transcription factors. As a homologous transcription factor, an amino acid sequence having, for example, 70% or higher, preferably 80% or higher, more preferably 90% or higher, and most preferably 95% or higher homology to the amino acid sequence of any of the above transcription factors is searched for. Homology values are determined by default using a computer program that implements the BLAST algorithm and a database that stores gene sequence information.

In case that the genome information of intended plants has not been revealed, the genome is extracted from the intended plant, or a cDNA library of the intended plant is constructed. The genome region or cDNA hybridizing under stringent conditions to at least part of the nucleotide sequence of the gene of transcription factor At3g15510, At5g24520, At5g07580, At1g74930, At5g47390, At5g25190, or At3g61910 is then isolated. Thus, a homologous gene can be identified. Under stringent conditions, hybridization is carried out via washing at 60° C. in the presence of 2×SSC while maintaining a bond. Hybridization can be carried out in accordance with a conventional technique, such as the method disclosed by J. Sambrook et al. Molecular Cloning, A Laboratory Manual, 2nd Ed., Cold Spring Harbor Laboratory, 1989.

The plant according to the present invention significantly improves the amount of fat and oil production via expression of the above-described transcription factor with suppressed transcription accelerating activity. In such plant, the endogenous transcription factor may be modified and transcription accelerating activity thereof may be suppressed. Alternatively, a gene encoding a modified transcription factor with suppressed transcription accelerating activity may be introduced and such gene may be expressed. Transcription accelerating activity of the gene encoding the target transcription factor may be suppressed via a so-called gene-silencing technique.

A preferable example of such technique is a technique comprising introducing a gene encoding a fusion protein resulting from the fusion of the aforementioned transcription factor with a functional peptide that converts an arbitrary transcription factor into a transcription repressor into an intended plant and expressing such fusion protein therein.

A functional peptide that converts an arbitrary transcription factor into a transcription repressor (hereafter referred to as a "transcription repressor converting peptide") used herein is not particularly limited, as long as it can form a chimeric protein fused with the transcription factor, thereby suppressing transcription of the target gene regulated by the transcription factor. Such transcription repressor converting peptide is described in detail in JP Patent Publication (kokai) No. 2005-204657 A, and all peptides disclosed therein can be used.

Examples of transcription repressor converting peptides include amino acid sequences represented by formulae (1) to (8) below:

$$X1\text{-Leu-Asp-Leu-}X2\text{-Leu-}X3 \qquad (1)$$

wherein X1 represents 0 to 10 amino acid residues; X2 represents Asn or Glu; and X3 represents at least 6 amino acid residues;

$$Y1\text{-Phe-Asp-Leu-Asn-}Y2\text{-}Y3 \qquad (2)$$

wherein Y1 represents 0 to 10 amino acid residues; Y2 represents Phe or Ile; and Y3 represents at least 6 amino acid residues;

$$Z1\text{-Asp-Leu-}Z2\text{-Leu-Arg-Leu-}Z3 \qquad (3)$$

wherein Z1 represents Leu, Asp-Leu, or Leu-Asp-Leu; Z2 represents Glu, Gln, or Asp; and Z3 represents 0 to 10 amino acid residues;

$$\text{Asp-Leu-}Z4\text{-Leu-Arg-Leu} \qquad (4)$$

wherein Z4 represents Glu, Gln, or Asp;

$$\alpha1\text{-Leu-}\beta1\text{-Leu-}\gamma1\text{-Leu;} \qquad (5)$$

$$\alpha1\text{-Leu-}\beta1\text{-Leu-}\gamma2\text{-Leu;} \qquad (6)$$

$$\alpha1\text{-Leu-}\beta2\text{-Leu-Arg-Leu; and} \qquad (7)$$

$$\alpha2\text{-Leu-}\beta1\text{-Leu-Arg-Leu} \qquad (8)$$

wherein, in formulae (5) to (8), α1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp.

Transcription Repressor Converting Peptide Represented by Formula (1)

The number of amino acid residues represented by X1 of the transcription repressor converting peptide represented by formula (1) may be 0 to 10. Specific types of amino acids that constitute the amino acid residues represented by X1 are not particularly limited, and any amino acid may be used. It is preferable that the number of amino acid residues represented by X1 be as small as possible from the viewpoint of ease of synthesis of the transcription repressor converting peptide represented by formula (1). Specifically, the number of amino acid residues represented by X1 is preferably 5 or less.

Also, the number of the amino acid residues represented by X3 of the transcription repressor converting peptide represented by formula (1) may be at least 6. Specific types of amino acids that constitute the amino acid residues represented by X3 are not particularly limited, and any amino acid may be used.

Transcription Repressor Converting Peptide Represented by Formula (2)

The number of the amino acid residues represented by Y1 of the transcription repressor converting peptide represented by formula (2) may be 0 to 10 as in the case of X1 of the transcription repressor converting peptide represented by formula (1). Also, specific types of amino acids that constitute the amino acid residues represented by Y1 are not particularly limited, and any amino acid may be used. Specifically, the number of amino acid residues represented by Y1 is preferably 5 or less.

Also, the number of the amino acid residues represented by Y3 of the transcription repressor converting peptide represented by formula (2) may be at least 6, as in the case of X3 of the transcription repressor converting peptide represented by formula (1). Also, specific types of amino acids that constitute the amino acid residues represented by Y3 are not particularly limited, and any amino acid may be used.

Transcription Repressor Converting Peptide Represented by Formula (3)

The amino acid residues represented by Z1 of the transcription repressor converting peptide represented by formula (3) comprise 1 to 3 Leu residues: i.e., Leu when the number of amino acids is 1; Asp-Leu when the number of amino acids is 2; and Leu-Asp-Leu when the number of amino acids is 3.

In contrast, the number of the amino acid residues represented by Z3 of the transcription repressor converting peptide represented by formula (3) may be 0 to 10. Also, specific types of amino acids that constitute the amino acid residues represented by Z3 are not particularly limited, and any amino acid may be used. Specifically, the number of amino acid residues represented by Z3 is more preferably 5 or less. Specific examples of amino acid residues represented by Z3 include, but are not limited to, Gly, Gly-Phe-Phe, Gly-Phe-Ala, Gly-Tyr-Tyr, and Ala-Ala-Ala.

The number of amino acid residues constituting the entire transcription repressor converting peptide represented by formula (3) is not particularly limited. From the viewpoint of ease of synthesis, the number of amino acids is preferably 20 or less.

Transcription Repressor Converting Peptide Represented by Formula (4)

The transcription repressor converting peptide represented by formula (4) is a hexamer (6-mer) comprising 6 amino acid residues. When the amino acid residue represented by Z4 of the transcription repressor converting peptide represented by formula (4) is Glue, the amino acid sequence of interest is equivalent to the amino acid sequence composed of amino acids 196 to 201 of the *Arabidopsis thaliana* SUPERMAN protein (SUP protein).

Various transcription repressor converting peptides described above can fuse to the above-described transcription factors to result in fusion proteins, and such peptides can convert the transcription factors into transcription repressors. According to the present invention, therefore, fusion proteins can be produced using polynucleotides encoding the transcription repressor converting peptides to obtain fusion genes thereof with genes encoding the transcription factors.

More specifically, polynucleotides encoding the transcription repressor converting peptides (hereafter referred to as the "transcription repressor converting polynucleotides") are ligated to the genes encoding the transcription factors to construct fusion genes, and the resulting fusion genes are introduced into plant cells. Thus, fusion proteins can be produced. Specific nucleotide sequences of the transcription repressor converting polynucleotides are not particularly limited, and such polynucleotides may comprise nucleotide sequences corresponding to the amino acid sequences of the transcription repressor converting peptides based on genetic codes. The transcription repressor converting polynucleotides may comprise nucleotide sequences that serve as ligation sites to be connected to the transcription factor genes, as necessary. When the amino acid reading frame of the transcription repressor converting polynucleotide is not aligned with that of the transcription factor gene, the polynucleotide may further comprise an additional nucleotide sequence, so as to align the reading frames. Further, the polynucleotide may comprise various additional polypeptides, such as a polypeptide having a linker function for connecting the transcription factor to the transcription repressor converting peptide or a polypeptide for labeling a fusion protein with an epitope, such as His, Myc, or Flag. Further, the fusion protein may comprise a structure other than a polypeptide, such as a sugar chain or an isoprenoid group, according to need.

The method for producing the plant according to the present invention is not particularly limited, provided that the method comprises a step of producing a transcription factor with suppressed transcription accelerating activity in a plant to improve the productivity of a fat and oil. An example thereof is a production method comprising steps of construction of an expression vector, transformation, and selection. Such steps are described in detail below.

Step of Constructing Expression Vector

A step of constructing an expression vector is not particularly limited, provided that a recombinant expression vector comprising the gene encoding the above-mentioned transcription factor, the transcription repressor converting polynucleotide, and a promoter is constructed. A variety of known vectors can be used as bases for recombinant expression vectors. Examples of vectors that can be used include plasmid, phage, and cosmid vectors, and adequate vectors can be selected in accordance with the plant cells to which such vectors are introduced or methods of introduction into a cell. Specific examples include pBR322, pBR325, pUC19, pUC119, pBluescript, pBluescriptSK, and pBI vectors. When a vector is introduced into plant by the *Agrobacterium* method, in particular, use of the pBI binary vector is preferable. Specific examples of pBI binary vectors include pBIG, pBIN19, pBI101, pBI121, and pBI221 vectors.

Promoters are not particularly limited, provided that such promoters can express a gene of interest in a plant. Known promoters can be preferably used. Examples of such promoters include cauliflower mosaic virus 35S promoters (CaMV 35S), actin promoters, ubiquitin promoters, noparin synthase promoters, tobacco PR1a gene promoters, and ribulose-1,5-bisphosphate carboxylase/oxygenase small subunit promoters in tomatoes. Among such promoters, cauliflower mosaic virus 35S promoters, actin promoters, and ubiquitin promoters are preferable. With the use of such promoters, arbitrary genes can be intensively expressed upon introduction of the resulting recombinant expression vector into plant cells. A promoter is ligated so as to express the fusion gene of the gene encoding the transcription factor with the transcription repressor converting polynucleotide, and the resultant may be introduced into the vector in that state. The specific structure of a recombinant expression vector is not particularly limited.

The recombinant expression vector may further comprise other DNA segments, in addition to the promoter and the fusion gene. Such other DNA segments are not particularly limited, and examples thereof include a terminator, a selection marker, an enhancer, and a nucleotide sequence for enhancing translation efficiency. Also, the recombinant expression vector may further comprise a T-DNA region. The T-DNA region can enhance the efficiency of gene introduction, particularly when introducing the recombinant expression vector into a plant with the use of *Agrobacterium*.

A terminator is not particularly limited, provided that it functions as a transcription termination site, and a known terminator may be used. Specific examples of terminators that can be preferably used include the transcription termination region of the noparin synthase gene (the Nos terminator) and the transcription termination region of the cauliflower mosaic virus 35S (the CaMV 35S terminator), with the Nos terminator being preferable. The recombinant vector can be used to avoid the occurrence of phenomena such as synthesis of an unnecessarily long transcript after the introduction thereof into plant cells or a reduction in the plasmid copy number caused by a potent promoter by positioning a terminator in an adequate site.

Drug-resistance genes can be used as selection markers, for example. Specific examples of such drug-resistance genes include drug-resistance genes that are resistant to hygromycin, bleomycin, kanamycin, gentamicin, and chloramphenicol. Plants that grow in a medium containing the above antibiotics may be selected with the use of such selection markers, so that transformed plants can be easily selected.

An example of a nucleotide sequence for enhancing translation efficiency is the omega sequence derived from the tobacco mosaic virus. This omega sequence may be located in the untranslational region (5' UTR) of the promoter to enhance the translation efficiency of the fusion gene. Thus, the recombinant expression vector can comprise a variety of DNA segments in accordance with its intended purposes.

Methods for constructing recombinant expression vectors are not particularly limited. The promoter, the gene encoding the transcription factor, the transcription repressor converting polynucleotide, and, according to need, other DNA segments may be introduced into an adequately selected matrix vector in a predetermined order. For example, the gene encoding the transcription factor may be ligated to the transcription repressor converting polynucleotide to construct a fusion gene, the fusion gene may then be ligated to the promoter (e.g., a terminator according to need) to construct an expression cassette, and the resulting expression cassette may be introduced into the vector.

When constructing a fusion gene and an expression cassette, for example, cleavage sites of DNA segments are made to be protruding ends that are complementary to each other, such DNA segments are subjected to the reaction with the aid of ligation enzymes, and the order of such DNA segments can be determined. When an expression cassette comprises a terminator, the expression cassette may comprise the promoter, the chimeric gene, and the terminator, in that order from upstream. Also, the types of reagents used for constructing a recombinant expression vector (i.e., restriction enzymes or ligation enzymes) are not particularly limited, and commercially available products may be adequately selected and used.

Also, methods for growing the recombinant expression vector (i.e., methods of production) are not particularly limited, and known methods can be employed. In general, *E. coli* hosts may be used, and the recombinant expression vector may be grown therein. In such a case, preferable *E. coli* species may be selected in accordance with a vector type.

Step of Transformation

The step of transformation that is carried out in the present invention comprises introducing the recombinant expression vector into a plant cell in order to express the aforementioned fusion genes. Methods of introducing a recombinant expression vector into a plant cell (i.e., methods of transformation) are not particularly limited, and adequate known methods can be employed in accordance with a given plant cell. Specific examples of such methods include a method involving the use of *Agrobacterium* and a method involving direct introduction of a recombinant expression vector into a plant cell. Examples of methods involving the use of *Agrobacterium* that can be employed include methods described in Bechtold, E., Ellis, J., and Pelletier, G., 1993, In *Planta Agrobacterium*-mediated gene transfer by infiltration of adult *Arabidopsis* plants, C. R. Acad. Sci. Paris Sci. Vie, 316, 1194-1199 and Zyprian E., Kado C. L., *Agrobacterium*-mediated plant transformation by novel mini-T vectors in conjunction with a high-copy vir region helper plasmid, Plant Molecular Biology, 1990, 15 (2), 245-256.

Examples of methods involving direct introduction of a recombinant expression vector into a plant cell include microinjection, electroporation, the polyethylene glycol method, the particle gun method, the protoplast fusion method, and the calcium phosphate method.

Examples of plant cells into which the recombinant expression vector is to be introduced include tissue cells in plant organs such as flowers, leaves, and roots, calluses, and suspension cultured cells. According to the method for producing plants according to the present invention, the recombinant expression vector may be adequately constructed in accordance with the type of plant to be produced. Alternatively, a general-purpose recombinant expression vector may be constructed in advance and it may be introduced into a plant cell. Specifically, the method for producing plants according to the present invention may or may not comprise the step of constructing the recombinant expression vector.

Other Steps and Other Methods

The method for producing the plant according to the present invention may comprise a method of transformation. Further, the method may comprise a method for constructing a recombinant expression vector and other steps. Specifically, the method may comprise a step of selecting adequate transformants from transformed plants.

Methods of selection are not particularly limited. For example, transformants may be selected based on, for example, drug resistance, such as hygromycin-resistance, or based on the content of fat and oil in plants or arbitrary organs or tissues after the transformed plants have been grown. For example, transformants may be selected based on fat and oil content by quantifying the fat and oil components in seeds of the transformants in accordance with a conventional technique and comparing the quantified value with the fat and oil content in seeds of non-transformed plants (see the examples below).

According to the method for producing the plant according to the present invention, the fusion gene is introduced into a plant. Thus, offspring plants exhibiting significantly improved fat and oil content can be obtained from such plant via sexual or asexual reproduction. Also, plant cells or reproductive materials, such as seeds, fruits, stocks, calluses, tubers, cut ears, or lumps, may be obtained from a plant or an offspring plant thereof, and a plant of interest can be mass-produced therefrom. The method for producing the plant according to the present invention, accordingly, may comprise a step of growing the selected plant (i.e., the step of mass production).

The term "plant" used herein refers to a grown plant, a plant cell, a plant tissue, a callus, or a seed. According to the present invention, specifically, substances that can eventually grow into individual plants are regarded as plants. Plant cells can exist in various forms. Examples of such plant cells include suspension cultured cells, protoplasts, and leaf sections. Such plant cells may be grown and differentiated to obtain plants. Plants can be reproduced from plant cells via a known technique in accordance with plant cell type. The method for producing the plant according to the present invention, accordingly, may comprise a step of reproducing plants from plant cells or the like.

The method for producing the plant according to the present invention is not limited to a method in which transformation is carried out with the aid of a recombinant expression vector, and other methods may be employed. Specifically, a fusion protein may be introduced into a plant, for example. In such a case, a fusion protein may be introduced into a young plant so as to improve the fat and oil content in a site of a plant that is to be eventually used. Methods for introducing a fusion protein are not particularly limited, and various known methods may be employed.

As described above, the present invention can provide a plant into which a transcription factor with suppressed transcription accelerating activity has been introduced and in which fat and oil content has been significantly improved. A transcription factor having transcription accelerating activity is also expressed in the plant according to the present invention; however, the transcription factor with suppressed transcription accelerating activity can suppress gene expression in a dominant-negative manner. This varies the expression levels of genes involved in fat and oil production and/or genes involved in decomposition of the produced fat and oil in the plant according to the present invention. This can result in the significantly enhanced fat and oil content.

The condition of "significantly enhanced fat and oil content" refers to a situation in which fat and oil content has been enhanced, although seed mass per grain has not changed compared with wild-type plants, or a situation in which fat and oil content has been enhanced with significantly increased seed mass per grain compared with wild-type plants. Both cases indicate increased amounts of fat and oil produced by an individual plant. The plant according to the present invention can be used for the method for producing plant-derived fat and oil. For example, the plant according to the present invention is allowed to grow, seeds are collected, and fat and oil components are extracted from the collected seeds. Thus, the fat and oil can be produced.

It can be said that the method for producing fat and oil utilizing the plant according to the present invention is excellent particularly in terms of productivity because of the high fat and oil content in an individual plant. If the number of cultivated plants is assumed to be constant per unit of cultivation area, specifically, the amount of fat and oil produced per unit of cultivation area is significantly increased with the use of the plant according to the present invention. With the use of the plant according to the present invention, accordingly, production costs required for the production of fat and oil can be remarkably reduced.

In the method for producing fat and oil using the plant according to the present invention, the fat and oil to be produced are not particularly limited. Examples thereof include plant-derived fat and oil, such as soybean oil, sesame oil, olive oil, coconut oil, rice oil, cottonseed oil, sunflower oil, corn oil, safflower oil, and rapeseed oil. The produced fat and oil can be extensively used for household or industrial applications. Further, such fat and oil can be used as starting materials for biodiesel fuels. With the use of the plant according to the present invention, specifically, such fat and oil for household or industrial applications, biodiesel fuels, and the like can be produced at low cost. An improved seed yield per plant can result in an improvement in the productivity of feeds and food products, in addition to the productivity of fat and oil, and production costs can be reduced. Also, an increased amount of biomass per plant can result in an improvement in the productivity of biomass after seed harvesting or the entire biomass. Biomass can be adequately treated to be degraded into sugar. Sugar can be converted into a variety of chemical substances, including ethanol, by a fermentation method utilizing microorganisms. Also, biomass may be directly combusted to obtain thermal energy or an electric energy may be obtained from the thermal energy. With the use of the plant provided by the present invention, chemical substances, thermal energy, electric energy, and the like described above can be produced in a cost-effective manner.

EXAMPLES

Hereafter, the present invention is described in greater detail with reference to the examples, although the technical scope of the present invention is not limited to the examples.

Example 1

In this example, fusion proteins of *Arabidopsis thaliana* transcription factors At3g15510, At5g24520, At5g07580, At1g74930, At5g47390, At5g25190, and At3g61910 to which repressor domain sequences had been added were expressed in plants, and the fat and oil content of the seeds obtained from the plants was measured.

Amplification of Transcription Factor Genes

The genes encoding the above-mentioned transcription factors were obtained from the *Arabidopsis thaliana* cDNA library, and the regions excluding the termination codons of such genes were amplified via PCR using the primers shown below. PCR was carried out via denaturation at 94° C. for 1 minute, annealing at 47° C. for 2 minutes, and elongation at 74° C. for 1 minute, and this cycle was repeated 25 times. After the completion of PCR, the amplified DNA fragment was separated via agarose gel electrophoresis and recovered.

```
Forward primer for amplifying At3g15510
                                    (SEQ ID NO: 15)
GATGGAGAGCACCGATTCTTCCGGTGGTCC Reverse primer for amplifying At3g15510
                                    (SEQ ID NO: 16)
AGAAGAGTACCAATTTAAACCGGGTAATT Forward primer for amplifying At5g24520
                                    (SEQ ID NO: 17)
GATGGATAATTCAGCTCCAGATTCGTTATC Reverse primer for amplifying At5g24520
                                    (SEQ ID NO: 18)
AACTCTAAGGAGCTGCATTTTGTTAGCAAA Forward primer for amplifying At5g07580
                                    (SEQ ID NO: 19)
ATGGCGAGTTTTGAGGAAAGC Reverse primer for amplifying At5g07580
                                    (SEQ ID NO: 20)
AAATGCATCACAGGAAGATGAAG Forward primer for amplifying At1g74930
                                    (SEQ ID NO: 21)
ATGGTGAAGCAAGCGATGAAGG Reverse primer for amplifying At1g74930
                                    (SEQ ID NO: 22)
AAAATCCCAAAGAATCAAAGATTC Forward primer for amplifying At5g47390
                                    (SEQ ID NO: 23)
GATGACTCGTCGATGTTCTCACTGCAATCA Reverse primer for amplifying At5g47390
                                    (SEQ ID NO: 24)
TAAAGCGTGTATCACGCTTTTGATGTCTGA Forward primer for amplifying At5g25190
                                    (SEQ ID NO: 25)
ATGGCACGACCACAACAACGC Reverse primer for amplifying At5g25190
                                    (SEQ ID NO: 26)
CAGCGTCTGAGTTGGTAAAACAG Forward primer for amplifying At3g61910
                                    (SEQ ID NO: 27)
GATGAACATATCAGTAAACGGACAGTCACA Reverse primer for amplifying At3g61910
                                    (SEQ ID NO: 28)
TCCACTACCGTTCAACAAGTGGCATGTCGT
```

Preparation of Fusion Genes

Fusion genes that encode fusion proteins of the above transcription factors each comprising a repressor domain sequence added to the C terminus were prepared. In order to add a polynucleotide encoding a repressor domain sequence to the 3' terminus of each of the DNA fragments amplified via PCR above, the p35SSXG vector having the SmaI site and a polynucleotide encoding the repressor domain sequence (GLDLDLELRLGFA) in a site downstream of the CaMV 35S promoter was first prepared. p35SSXG was cleaved with SmaI and the DNA fragments amplified via PCR above were inserted thereinto. The resulting expression vectors were designated as p35SSXG (At3g15510), p35SSXG (At5g24520), p35SSXG (At5g07580), p35SSXG (At1g74930), p35SSXG (At5g47390), p35SSXG (At5g25190), and p35SSXG (At3g61910).

Construction of Binary Vectors

A pBCKH binary vector was used in order to transform a plant by the *Agrobacterium* method. This vector was prepared by incorporating a cassette of the Gateway vector conversion system (Invitrogen) into the HindIII site of pBIG (Hygr) (Nucleic Acids Res. 18, 203, 1990). In order to incorporate the fusion gene into this vector, the vector was mixed with p35SSXG (At3g25890) or p35SSXG (At1g56650), and a recombination reaction was carried out using GATEWAY LR clonase (Invitrogen). As a result, pBCKH-p35SSXG (At3g15510), pBCKH-p35SSXG (At5g24520), pBCKH-p35SSXG (At5g07580), pBCKH-p35SSXG (At1g74930), pBCKH-p35SSXG (At5g47390), pBCKH-p35SSXG (At5g25190), and pBCKH-p35SSXG (At3g61910) were constructed.

Introduction of Binary Vector into Plant

In this example, *Arabidopsis thaliana* of Brassicaceae (*Arabidopsis thaliana*, Columbia) was used. Gene introduction was carried out in accordance with the method described in Bechtold, E., Ellis, J., and Pelletier, G., 1993, *In Planta*

Agrobacterium-mediated gene transfer by infiltration of adult Arabidopsis plants, C. R. Acad. Sci. Paris Sci. Vie, 316, 1194-1199 and Zyprian E., Kado C. L., Agrobacterium-mediated plant transformation by novel mini-T vectors in conjunction with a high-copy vir region helper plasmid, Plant Molecular Biology, 1990, 15 (2), 245-256. Plants were infected via soaking in the Agrobacterium solution without depressurization. Specifically, the binary vectors constructed above were introduced into soil bacteria (i.e., the Agrobacterium tumefaciens strain GV3101 (C58C1Rifr) pMP90 (Gmr)) (koncz and Schell, 1986) via electroporation. The introduced bacteria were cultured in 1 liter of YEP medium containing antibiotics (50 µg/ml of kanamycin (Km), 25 µg/ml of gentamicin (Gm), and 50 µg/ml of rifampicin (Rif)) until OD600 reached 1. Subsequently, the bacteria were recovered from the culture solution and suspended in 1 liter of infiltration medium (containing 2.2 g of MS salt, 1×B5 vitamins, 50 g of sucrose, 0.5 g of MES, 0.044 µM of benzylaminopurine, and 400 µl of Silwet per liter; pH: 5.7).

The Arabidopsis thaliana plant that had been grown for 14 days was soaked in this solution for 1 minute, the plant was infected, and culture was continued again for fructification. The resulting seeds (T1 seeds) were sterilized with a 50% bleach/0.02% Triton X-100 solution for 7 minutes, the seeds were rinsed three times with sterilized water, and the seeds were sowed on the sterilized hygromycin selection medium (4.3 g/1 MS salts, 0.5% sucrose, 0.5 g/1 MES (pH 5.7), 0.8% agar, 30 mg/1 hygromycin, and 250 mg/1 vancomycin). Ten transformed strains that had grown on the hygromycin plate (T1 plants) were selected per modified transcription gene and transferred to a pot (diameter: 50 mm) containing vermiculite composite soils. The transformants were cultivated at 22° C. for 16 hours in the light and 8 hours in the dark at an optical intensity of about 60 to 80 µE/cm² to obtain seeds (T2 seeds).

<Analysis of T2 Seeds>

Quantitative analysis of fat and oil components in the resulting T2 seeds was carried out using MARAN-23 (Resonance Instruments Ltd., UK) $^H$-NMR and the RI-NMR Ver. 2.0 analysis software. With the use of such apparatuses, 2 to 10 mg of T2 seeds were measured. A calibration curve was prepared using olive oil as the fat and oil reference material and the fat and oil content in the seeds (% by weight) was determined.

Single seed weight was measured by weighing about 1 mg of T2 seeds, spreading the T2 seeds on a glass petri dish, scanning the image of seeds using Pictrostat (Fujifilm), gray-scale processing the image using Photoshop image-editing software, analyzing the gray-scale image using Scion Image image-analyzing software, and determining the number of seeds. The total seed weight was divided by the number of seeds, and the seed weight per grain was determined. The fat and oil components of wild-type Arabidopsis thaliana were similarly quantified. The results are summarized in Table 2.

TABLE 2

| Name of introduced gene | Fat and oil content | | Single seed weight | | Fat and oil amount per grain | |
|---|---|---|---|---|---|---|
| | Content (%) | Percentage of increase in fat and oil content | Weight (µg) | Percentage of increase in weight | Amount of fat and oil (µg/grain) | Percentage of increase |
| WT | 34.3% | | 19.8 | | 6.8 | |
| At3g15510-SRDX | 42.4% | 23.7% | 20.4 | 3.1% | 8.64 | 26.9% |
| At5g24510-SRDX | 42.3% | 23.4% | 19.8 | 0.3% | 8.39 | 23.2% |
| At5g07580-SRDX | 42.2% | 23.2% | 18.2 | −7.8% | 7.69 | 13.0% |
| At1g74930-SRDX | 42.0% | 22.5% | 18.8 | −4.8% | 7.90 | 16.0% |
| At5g47390-SRDX | 41.2% | 20.2% | 27.3 | 38.2% | 11.25 | 65.2% |
| At5g25190-SRDX | 41.2% | 20.1% | 25.3 | 28.3% | 10.44 | 53.3% |
| At3g61910-SRDX | 41.2% | 20.1% | 17.6 | −10.7% | 7.26 | 6.6% |

As is apparent from Table 2, the percentage of increase in the fat and oil amount per grain is significantly increased in all the plants prepared in the examples, compared with wild-type plants. The plants into which the transcription factor At5g47390 with suppressed transcription accelerating activity had been introduced and the plants into which the transcription factor At5g25190 with suppressed transcription accelerating activity had been introduced exhibited excellent percentages of increase in the fat and oil amount per grain.

As is apparent from Table 2, the fat and oil content in seeds of control wild-type plants into which no gene had been introduced was 34.3% and the single seed weight thereof was 19.8 µg. In contrast, the fat and oil content in seeds of all the plants prepared in the examples was increased by 20% or more from that in wild-type plants. Three strains (i.e., At3g15510-SRDX, At5g24520-SRDX, and At5g07580-SRDX) exhibited an increase in the fat and oil content of 23% or more.

The above results demonstrate that the plants into which the transcription factors with suppressed expression accelerating activity had been introduced exhibit the excellent fat and oil content per grain and such plants are thus very effective for fat and oil production.

<Analysis of T3 Seeds>

In order to analyze T3 seeds, the T2 plants prepared as above were cultivated via two separate experiments. Because of different illumination conditions resulting from the different positions of cultivation trays, test plants and control plants were simultaneously cultivated in the same cultivation tray, and the results were compared.

Experiment 1) After the T2 seeds were sterilized with a 50% bleach/0.02% Triton X-100 solution for 7 minutes, the seeds were rinsed three times with sterilized water, and the seeds were sowed on the sterilized seeding medium (4.3 g/1 MS salts, 0.5% sucrose (pH 5.7), 0.8% agar, and 10 mg/1 hygromycin). Three weeks after seeding, 4 each transformed plants (T1 plants) into which the modified transcriptional genes had been introduced were transferred to a pot (diameter: 50 mm) containing vermiculite composite soils. As controls, 2 non-recombinant Arabidopsis thaliana plants were transferred. Each strain of the plants was separately introduced into cultivation trays and cultivated at 22° C. for 16 hours in the light and 8 hours in the dark at an optical intensity of about 30 to 45 µE/cm², and, 4 weeks thereafter, the plants were subjected to thinning out while leaving 4 recombinant plants and 3 non-recombinant plants behind. The plants were cultivated for an additional 7 weeks until 11 weeks after the transfer.

Experiment 2) Seeds were sterilized, sowed on plates, and grown in the same manner as in Experiment 1), and 6 each transformed plants (T1 plants) into which the modified transcriptional genes had been introduced were transferred to a pot (diameter: 50 mm) containing vermiculite composite soils. Cultivation was carried out in the same manner as in Experiment 1), and the plants were cultivated until 11 weeks after the transfer.

Measurement and analysis) The aerial parts of the plants were introduced into a paper bag and dried at 22° C. and humidity of 60% for 2 weeks. Thereafter, total biomass amount and seed yield were weighed using an electronic balance. Quantitative analysis of fat and oil was carried out by the method described above.

Figure 2:
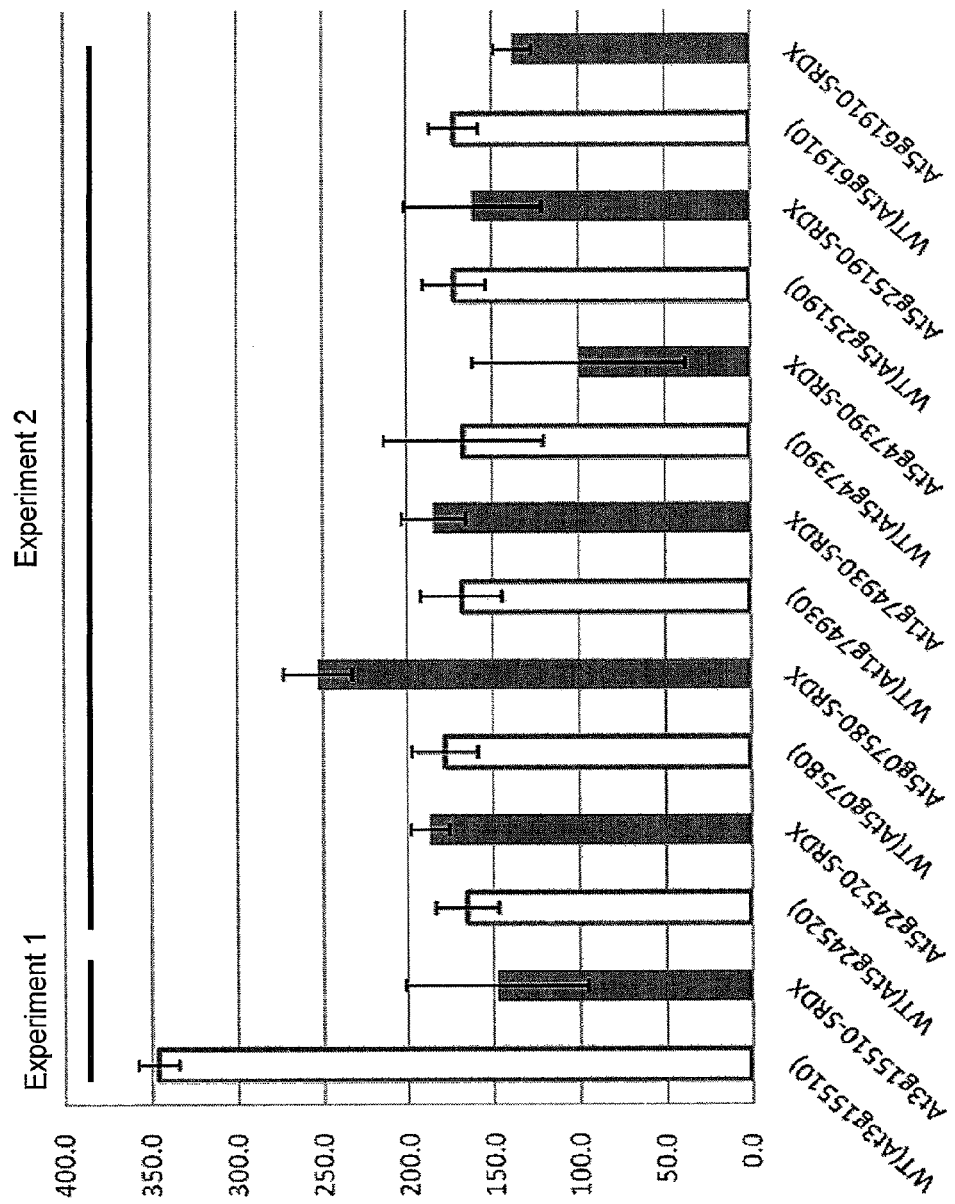
FIG. 2 is a characteristic diagram showing the results of measuring the seed yields of plants prepared in the examples (T2 plant-T3 seeds).
Figure 3:
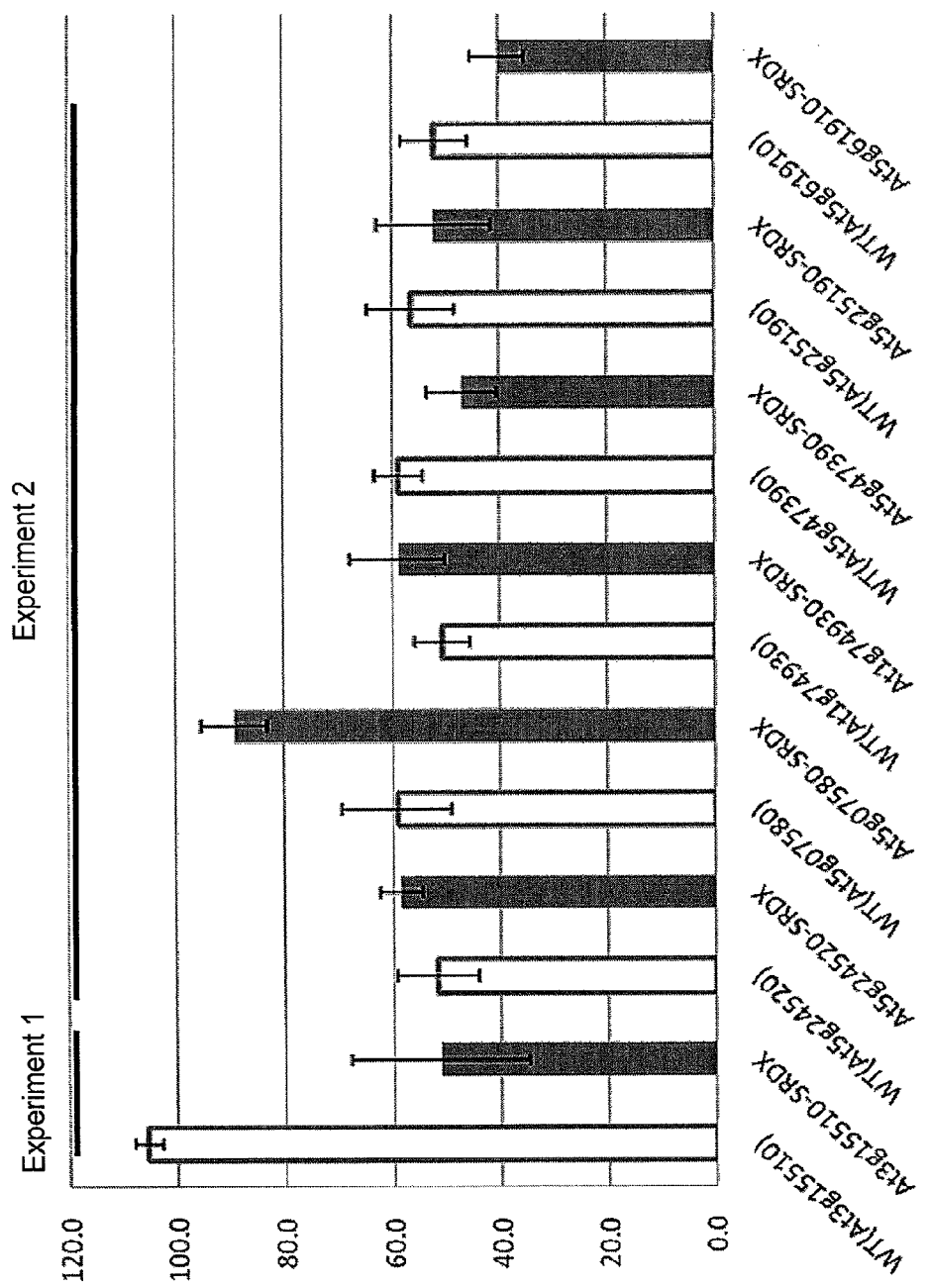
FIG. 3 is a characteristic diagram showing the results of calculating the amount of fat and oil production per individual plant of plants prepared in the examples (T2 plant-T3 seeds).
Figure 4:
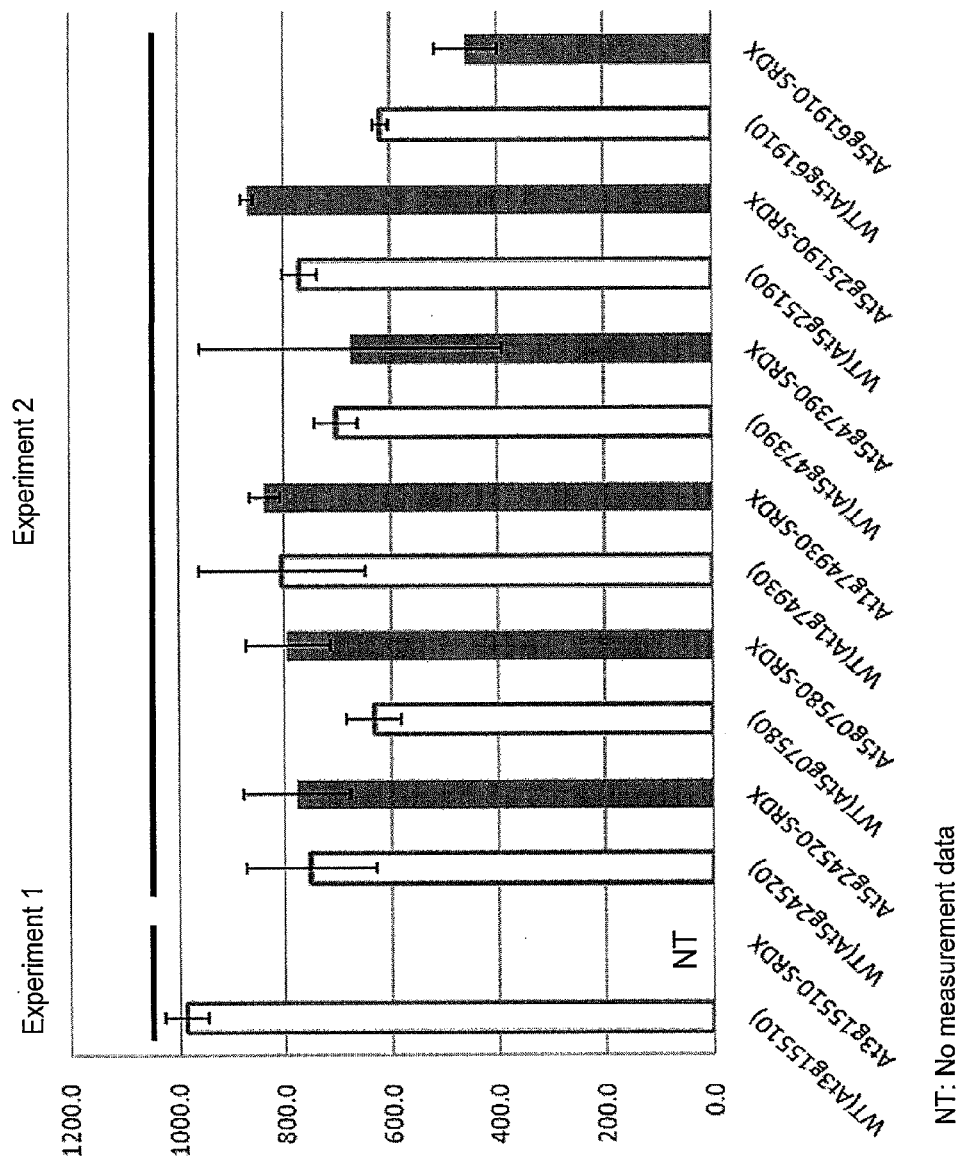
FIG. 4 is a characteristic diagram showing the results of measuring the amount of biomass of plants prepared in the examples (T2 plant-T3 seeds).

FIG. 1 shows the results of measuring the fat and oil content of T3 seeds. The fat and oil contents in the seeds obtained from the control wild type (WT) plant was not consistent with the results of measurement of T2 seeds, which had been cultivated under different conditions. The test strains into which the transcription factors At5g24520-SRDX, At5g07580-SRDX, and At5g61910-SRDX with suppressed expression accelerating activity had been introduced exhibited higher fat and oil contents in seeds than the control strains. FIG. 2 shows the seed yields. The strain into which At5g07580-SRDX had been introduced exhibited the seed yield increased by about 42% from that of the control strain. The amount of fat and oil production per plant was calculated based on the product of the seed yield and the fat and oil content, and the results are shown in FIG. 3. The strain into which At5g07580-SRDX had been introduced exhibited a significantly higher fat and oil content per plant than the control WT strain. FIG. 4 shows the results of measuring the total biomass amount of the aerial parts including seeds. The strains into which the transcription factors At5g07580-SRDX and At5g25190-SRDX with suppressed transcription accelerating activity had been introduced exhibited a significantly higher total biomass amount than control WT strains.

Table 3 shows the percentage of increase/decrease in fat and oil content, seed yield, fat and oil amount per plant, and biomass amount of recombinant test strains into which the transcription factor genes with the regulated transcription accelerating activity had been introduced by designating the values of the control strains as 100%.

TABLE 3

| Tested strain | Percentage of increase/decrease (relative to the control = 100%) | | | |
| --- | --- | --- | --- | --- |
| | Fat and oil content | Seed yield | Fat and oil amount per plant | Biomass amount |
| At3g15510-SRDX | 100% | 43% | 49% | — |
| At5g24520-SRDX | 109% | 113% | 113% | 104% |
| At5g07580-SRDX | 114% | 142% | 151% | 125% |
| At1g74930-SRDX | 105% | 110% | 116% | 104% |
| At5g47390-SRDX | 67% | 60% | 80% | 96% |
| At5g25190-SRDX | 83% | 94% | 93% | 113% |
| At5g61910-SRDX | 109% | 80% | 78% | 74% |

When the T2 generation is compared with the T3 generation, the above results occasionally show differences in fat and oil content per plant, seed yield, fat and oil content, and the amount of biomass. Because of the application of Mendel's law for the case of the difference between the T2 generation and the T3 generation, the T2 generation and the T3 generation do not always have the same genotype. Since mRNA may suppress gene expression as is known in the case of the RNAi technique, also, differences occur between the T2 generation and the T3 generation. The plants into which any of the transcription factor At3g15510, At5g24520, At5g07580, At1g74930, At5g47390, At5g25190, or At3g61910 with suppressed expression accelerating activity had been introduced can be evaluated as exhibiting excellent effects in terms of increased biomass amount, increased seed yield, and increased fat and oil yield.

Example 2

In Example 2, a fusion protein of the *Arabidopsis thaliana* transcription factor At5g07580 to which a repressor domain sequence had been added was expressed in plants as in the case of Example 1, and the fat and oil content in seeds obtained from rice of graminaceous monocotyledonous plants (*Olyza sative* Nipponbare) was measured.

Amplification of Transcription Factor Gene, Preparation of Fusion Gene, and Construction of Binary Vector Amplification of the transcription factor gene, preparation of the fusion gene, and construction of the binary vector were carried out in the same manner as in Example 1.

Introduction of Binary Vector into Plant

A binary vector was introduced into rice plants (Nipponbare) using *Agrobacterium* carrying the binary vector in accordance with the method described in JP Patent No. 3141084 to obtain calluses.

The calluses into which the gene had been introduced were subjected to selection with hygromycin at 50 ppm for a month, and calluses exhibiting drug resistance were obtained. DNA was prepared from the obtained calluses in accordance with a conventional technique. The At5g07580 fusion gene was confirmed via PCR using the prepared DNA as a template. The calluses having drug-resistance phenotypes and containing the At5g07580 fusion gene were transferred to a redifferentiation medium (described in JP Patent No. 3141084) to induce redifferentiation, and the resultant was then transferred to a hormone-free MS medium (described in JP Patent No. 3141084) to obtain transformed plants.

The transformed plants were grown for 16 hours in the light (photon amount: 135 µE/cm$^2$; temperature: 30° C.) and for 8 hours in the dark (temperature: 25° C.) for 100 days. Thereafter, the plants were further grown for 12 hours in the light (photon amount: 135 µE/cm$^2$; temperature: 30° C.) and for 12 hours in the dark (temperature: 25° C.), and the fructified seeds (T1 seeds) were recovered.

Analysis of T1 Seeds

Fat and oil in the resulting rice T1 seeds was quantitatively analyzed in the same manner as in <Analysis of T2 seeds> in Example 1. Since the rice seed weight is about 20 mg per brown rice grain, the fat and oil content in a grain was quantified with good reproducibility. The results are shown in Table 4. Brown rice is a seed containing a pericarp, a seed coat, an albumen, and an aleurone layer, and caryopsis is a so-called hull.

TABLE 4

| Name of introduced gene | Name of strain | Tissue | Fat and oil content | | Single seed weight | | Fat and oil amount per grain | |
|---|---|---|---|---|---|---|---|---|
| | | | Content (%) | Percentage of increase | Weight (mg) | Percentage of increase | Fat and oil amount (mg) | Percentage of increase |
| WT (average of 5 grains) | | Brown rice | 2.17 | — | 20.90 | — | 0.454 | — |
| At5g07580-SRDX | CR035-10-5 | Brown rice | 1.93 | −11.1% | 24.01 | 14.9% | 0.463 | 2.2% |
| At5g07580-SRDX | CR035-15-2 | Brown rice | 3.10 | 42.9% | 17.92 | −14.3% | 0.556 | 22.5% |
| At5g07580-SRDX | CR035-18-2 | Brown rice | 3.14 | 44.7% | 16.37 | −21.7% | 0.514 | 13.3% |
| WT (average of 5 grains) | | Caryopsis | 5.91 | — | 3.99 | — | 0.236 | — |
| At5g07580-SRDX | CR035-10-5 | Caryopsis | 5.88 | −3.9% | 4.65 | 16.5% | 0.264 | 12.0% |
| At5g07580-SRDX | CR035-12-1 | Caryopsis | 7.63 | 29.1% | 4.56 | 14.3% | 0.348 | 47.5% |
| At5g07580-SRDX | CR035-20-3 | Caryopsis | 10.35 | 75.1% | 2.76 | −30.8% | 0.266 | 21.1% |

As is apparent from Table 4, graminaceous monocotyledonous plants into which the transcription factor At5g07580 with suppressed expression accelerating activity had been introduced exhibited a fat and oil content much higher than that of wild-type plants. Such transformed plants exhibited the excellent percentages of increase in fat and oil content per grain of 44.7% in brown rice and 75.1% in caryopsis, the excellent percentages of increase in the seed weight of 14.9% in brown rice and 16.5% in caryopsis, and the excellent percentages of increase in the fat and oil amount per seed grain of 22.5% in brown rice and 47.5% in caryopsis.

All publications, patents, and patent applications cited herein are incorporated herein by reference in their entirety.

The invention claimed is:

1. A plant which expresses a chimeric protein, said chimeric protein comprising a transcription factor fused to a repressor domain sequence that converts said transcription factor into a transcription repressor,
wherein said transcription factor is a protein comprising the amino acid sequence of SEQ ID NO: 10, or a protein comprising the amino acid sequence of SEQ ID NO: 10 but in which 1-20 amino acids have been deleted, substituted, added or inserted,
and wherein the seeds of said plant exhibit an increase in weight, an increase in amount of fat and oil, or an increase in fat and oil content, in comparison to a wild-type plant not expressing said chimeric protein.

2. The plant according to claim 1, wherein the repressor domain sequence comprises an amino acid sequence selected from the group consisting of (1) to (8):

(1) X1-Leu-Asp-Leu-X2-Leu-X3 (SEQ ID NO: 29 with deletion of 0-10 residues from the N-terminus)
wherein X1 represents 0 to 10 amino acid residues; X2 represents Asn or Glu; and X3 represents at least 6 amino acid residues;

(2) Y1-Phe-Asp-Leu-Asn-Y2-Y3 (SEQ ID NO: 30 with deletion of 0-10 residues from the N-terminus)
wherein Y1 represents 0 to 10 amino acid residues; Y2 represents Phe or Ile; and Y3 represents at least 6 amino acid residues;

(3) Z1-Asp-Leu-Z2-Leu-Arg-Leu-Z3 (SEQ ID NO: 31 with deletion of 0-10 residues from the C-terminus and deletion of 0-2 residues from the N-terminus)
wherein Z1 represents Leu, Asp-Leu, or Leu-Asp-Leu; Z2 represents Glu, Gln, or Asp; and Z3 represents 0 to 10 amino acid residues;

(4) Asp-Leu-Z4-Leu-Arg-Leu (SEQ ID NO: 32)
wherein Z4 represents Glu, Gln, or Asp;

(5) α1-Leu-β1-Leu-γ1-Leu; (SEQ ID NO: 33)

(6) α1-Leu-β1-Leu-γ2-Leu; (SEQ ID NO: 34)

(7) α1-Leu-β2-Leu-Arg-Leu; (SEQ ID NO: 35)
and (8) α2-Leu-β1-Leu-Arg-Leu; (SEQ ID NO: 36)

wherein, in formulae (5) to (8), α1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp.

3. A method for producing a plant in which the seeds of said plant exhibit an increase in weight, an increase in amount of fat and oil, or an increase in fat and oil content, said method comprising the step of expressing a chimeric protein in a plant, said chimeric protein comprising a transcription factor fused to a repressor domain sequence that converts said transcription factor into a transcription repressor,
wherein said transcription factor is a protein comprising the amino acid sequence of SEQ ID NO: 10, or a protein comprising the amino acid sequence of SEQ ID NO: 10 but in which 1-20 amino acids have been deleted, substituted, added or inserted, and wherein the seeds of said plant exhibit an increase in weight, an increase in amount of fat and oil, or an increase in fat and oil content, in comparison to a wild-type plant not expressing said chimeric protein.

4. The method for producing a plant according to claim 3, wherein the repressor domain sequence comprises an amino acid sequence selected from the group consisting of (1) to (8):

(1) X1-Leu-Asp-Leu-X2-Leu-X3 (SEQ ID NO: 29 with deletion of 0-10 residues from the N-terminus)
wherein X1 represents 0 to 10 amino acid residues; X2 represents Asn or Glu; and X3 represents at least 6 amino acid residues;

(2) Y1-Phe-Asp-Leu-Asn-Y2-Y3 (SEQ ID NO: 30 with deletion of 0-10 residues from the N-terminus)
wherein Y1 represents 0 to 10 amino acid residues; Y2 represents Phe or Ile; and Y3 represents at least 6 amino acid residues;

(3) Z1-Asp-Leu-Z2-Leu-Arg-Leu-Z3 (SEQ ID NO: 31 with deletion of 0-10 residues from the C-terminus and deletion of 0-2 residues from the N-terminus)
wherein Z1 represents Leu, Asp-Leu, or Leu-Asp-Leu; Z2 represents Glu, Gln, or Asp; and Z3 represents 0 to 10 amino acid residues;

(4) Asp-Leu-Z4-Leu-Arg-Leu (SEQ ID NO: 32)

wherein Z4 represents Glu, Gln, or Asp;

(5) α1-Leu-β1-Leu-γ1-Leu; (SEQ ID NO: 33)

(6) α1-Leu-β1-Leu-γ2-Leu; (SEQ ID NO: 34)

(7) α1-Leu-β2-Leu-Arg-Leu; (SEQ ID NO: 35)
and (8) α2-Leu-β1-Leu-Arg-Leu, (SEQ ID NO: 36)

wherein, in formulae (5) to (8), α1 represents Asp, Asn, Glu, Gln, Thr, or Ser; α2 represents Asn, Glu, Gln, Thr, or Ser; β1 represents Asp, Gln, Asn, Arg, Glu, Thr, Ser, or His; β2 represents Asn, Arg, Thr, Ser, or His; γ1 represents Arg, Gln, Asn, Thr, Ser, His, Lys, or Asp; and γ2 represents Gln, Asn, Thr, Ser, His, Lys, or Asp.

5. A method for isolating fat and oil from a plant, comprising separating and recovering fat and oil from the seeds of a plant which expresses a chimeric protein, wherein said chimeric protein comprises a transcription factor fused to a repressor domain sequence that converts said transcription factor into a transcription repressor,
wherein said transcription factor is a protein comprising the amino acid sequence of SEQ ID NO: 10, or a protein comprising the amino acid sequence of SEQ ID NO: 10 but in which 1-20 amino acids have been deleted, substituted, added or inserted,
and wherein the seeds of said plant exhibit an increase in weight, an increase in amount of fat and oil, or an increase in fat and oil content, in comparison to a wild-type plant not expressing said chimeric protein.

6. A chimeric protein comprising a transcription factor fused to a repressor domain sequence that converts said transcription factor into a transcription repressor,
wherein said transcription factor is a protein comprising the amino acid sequence of SEQ ID NO: 10, or a protein comprising the amino acid sequence of SEQ ID NO: 10 but in which 1-20 amino acids have been deleted, substituted, added or inserted,
and wherein when said chimeric protein is expressed in a plant, said plant produces seeds that exhibit an increase in weight, an increase in amount of fat and oil, or an increase in fat and oil content, in comparison to a wild-type plant not expressing said chimeric protein.

7. A polynucleotide encoding the chimeric protein according to claim 6.

8. A recombinant expression vector comprising the polynucleotide according to claim 7 and a promoter.

9. A kit comprising the expression vector according to claim 8.

10. The kit according to claim 9, wherein said kit further comprises reagents for introducing the recombinant expression vector into a plant cell.

* * * * *

SEQUENCE LISTING

<160> NUMBER OF SEQ ID NOS: 37

<210> SEQ ID NO 1
<211> LENGTH: 1095
<212> TYPE: DNA
<213> ORGANISM: Arabidopsis thaliana
<220> FEATURE:
<221> NAME/KEY: CDS
<222> LOCATION: (1)..(1095)

<400> SEQUENCE: 1

```
atg gag agc acc gat tct tcc ggt ggt cca cca ccg cca caa cct aac        48
Met Glu Ser Thr Asp Ser Ser Gly Gly Pro Pro Pro Pro Gln Pro Asn
1               5                   10                  15 ctt cct cca ggc ttc cgg ttt cac cct acc gac gaa gag ctt gtt gtt        96
Leu Pro Pro Gly Phe Arg Phe His Pro Thr Asp Glu Glu Leu Val Val
            20                  25                  30 cac tac ctc aaa cgc aaa gca gcc tct gct cct tta cct gtc gcc atc       144
His Tyr Leu Lys Arg Lys Ala Ala Ser Ala Pro Leu Pro Val Ala Ile
        35                  40                  45 atc gcc gaa gtc gat ctc tat aaa ttt gat cca tgg gaa ctt ccc gct       192
Ile Ala Glu Val Asp Leu Tyr Lys Phe Asp Pro Trp Glu Leu Pro Ala
    50                  55                  60 aaa gca tcg ttt gga gaa caa gaa tgg tac ttc ttt agt cca cga gat       240
Lys Ala Ser Phe Gly Glu Gln Glu Trp Tyr Phe Phe Ser Pro Arg Asp
65                  70                  75                  80 cgg aag tat cca aac gga gca aga cca aac aga gcg gcg act tca ggt       288
Arg Lys Tyr Pro Asn Gly Ala Arg Pro Asn Arg Ala Ala Thr Ser Gly
                85                  90                  95 tat tgg aaa gcg acc ggt aca gat aaa ccg gta ctt gct tcc gac ggt       336
Tyr Trp Lys Ala Thr Gly Thr Asp Lys Pro Val Leu Ala Ser Asp Gly
            100                 105                 110 aac caa aag gtg ggc gtg aag aag gca cta gtc ttc tac agt ggt aaa       384
Asn Gln Lys Val Gly Val Lys Lys Ala Leu Val Phe Tyr Ser Gly Lys
        115                 120                 125 cca cca aaa ggc gtt aaa agt gat tgg atc atg cat gag tat cgt ctc       432
Pro Pro Lys Gly Val Lys Ser Asp Trp Ile Met His Glu Tyr Arg Leu
    130                 135                 140 atc gaa aac aaa cca aac aat cga cct cct ggc tgt gat ttc ggc aac       480
Ile Glu Asn Lys Pro Asn Asn Arg Pro Pro Gly Cys Asp Phe Gly Asn
```

|   |   |   |   |   |   |   |   |   |   |   |   |   |   |   |   |      |
|---|---|---|---|---|---|---|---|---|---|---|---|---|---|---|---|------|
|   |   | 145 |   |   |   | 150 |   |   |   | 155 |   |   |   | 160 |   |      |
| aaa | aaa | aac | tca | ctc | aga | ctt | gat | gat | tgg | gtg | tta | tgt | aga | atc | tac | 528  |
| Lys | Lys | Asn | Ser | Leu | Arg | Leu | Asp | Asp | Trp | Val | Leu | Cys | Arg | Ile | Tyr |      |
|   |   |   |   | 165 |   |   |   | 170 |   |   |   | 175 |   |   |   |      |
| aag | aag | aac | aac | gca | agt | cga | cat | gtt | gat | aac | gat | aag | gat | cat | gat | 576  |
| Lys | Lys | Asn | Asn | Ala | Ser | Arg | His | Val | Asp | Asn | Asp | Lys | Asp | His | Asp |      |
|   |   |   | 180 |   |   |   | 185 |   |   |   | 190 |   |   |   |   |      |
| atg | atc | gat | tac | att | ttc | agg | aag | att | cct | ccg | tct | tta | tca | atg | gcg | 624  |
| Met | Ile | Asp | Tyr | Ile | Phe | Arg | Lys | Ile | Pro | Pro | Ser | Leu | Ser | Met | Ala |      |
|   |   | 195 |   |   |   | 200 |   |   |   | 205 |   |   |   |   |   |      |
| gct | gct | tct | aca | gga | ctt | cac | caa | cat | cat | cat | aat | gtc | tca | aga | tca | 672  |
| Ala | Ala | Ser | Thr | Gly | Leu | His | Gln | His | His | His | Asn | Val | Ser | Arg | Ser |      |
|   | 210 |   |   |   | 215 |   |   |   | 220 |   |   |   |   |   |   |      |
| atg | aat | ttc | ttc | cct | ggc | aaa | ttc | tcc | ggt | ggt | ggt | tac | ggg | att | ttc | 720  |
| Met | Asn | Phe | Phe | Pro | Gly | Lys | Phe | Ser | Gly | Gly | Gly | Tyr | Gly | Ile | Phe |      |
| 225 |   |   |   | 230 |   |   |   | 235 |   |   |   | 240 |   |   |   |      |
| tct | gac | ggt | ggt | aac | acg | agt | ata | tac | gac | ggc | ggt | ggc | atg | atc | aac | 768  |
| Ser | Asp | Gly | Gly | Asn | Thr | Ser | Ile | Tyr | Asp | Gly | Gly | Gly | Met | Ile | Asn |      |
|   |   |   |   | 245 |   |   |   | 250 |   |   |   | 255 |   |   |   |      |
| aat | att | ggt | act | gac | tca | gta | gat | cac | gac | aat | aac | gct | gac | gtc | gtt | 816  |
| Asn | Ile | Gly | Thr | Asp | Ser | Val | Asp | His | Asp | Asn | Asn | Ala | Asp | Val | Val |      |
|   |   |   | 260 |   |   |   | 265 |   |   |   | 270 |   |   |   |   |      |
| ggt | tta | aat | cat | gct | tcg | tcg | tca | ggt | cct | atg | atg | atg | gcg | aat | ttg | 864  |
| Gly | Leu | Asn | His | Ala | Ser | Ser | Ser | Gly | Pro | Met | Met | Met | Ala | Asn | Leu |      |
|   |   | 275 |   |   |   | 280 |   |   |   | 285 |   |   |   |   |   |      |
| aaa | cga | act | ctc | ccg | gtg | ccg | tat | tgg | cct | gta | gca | gat | gag | gag | caa | 912  |
| Lys | Arg | Thr | Leu | Pro | Val | Pro | Tyr | Trp | Pro | Val | Ala | Asp | Glu | Glu | Gln |      |
|   | 290 |   |   |   | 295 |   |   |   | 300 |   |   |   |   |   |   |      |
| gat | gca | tct | ccg | agc | aaa | cgg | ttt | cac | ggt | gta | gga | gga | gga | gga | gga | 960  |
| Asp | Ala | Ser | Pro | Ser | Lys | Arg | Phe | His | Gly | Val | Gly | Gly | Gly | Gly | Gly |      |
| 305 |   |   |   | 310 |   |   |   | 315 |   |   |   | 320 |   |   |   |      |
| gat | tgt | tcg | aac | atg | tct | tcc | tcc | atg | atg | gaa | gag | act | cca | cca | ttg | 1008 |
| Asp | Cys | Ser | Asn | Met | Ser | Ser | Ser | Met | Met | Glu | Glu | Thr | Pro | Pro | Leu |      |
|   |   |   |   | 325 |   |   |   | 330 |   |   |   | 335 |   |   |   |      |
| atg | caa | caa | caa | ggt | ggt | gtg | tta | gga | gat | gga | tta | ttc | aga | acg | aca | 1056 |
| Met | Gln | Gln | Gln | Gly | Gly | Val | Leu | Gly | Asp | Gly | Leu | Phe | Arg | Thr | Thr |      |
|   |   |   | 340 |   |   |   | 345 |   |   |   | 350 |   |   |   |   |      |
| tcg | tac | caa | tta | ccc | ggt | tta | aat | tgg | tac | tct | tct | taa |   |   |   | 1095 |
| Ser | Tyr | Gln | Leu | Pro | Gly | Leu | Asn | Trp | Tyr | Ser | Ser |   |   |   |   |      |
|   |   | 355 |   |   |   | 360 |   |   |   |   |   |   |   |   |   |      |

<210> SEQ ID NO 2
<211> LENGTH: 364
<212> TYPE: PRT
<213> ORGANISM: Arabidopsis thaliana

<400> SEQUENCE: 2

Met Glu Ser Thr Asp Ser Ser Gly Gly Pro Pro Pro Gln Pro Asn
1               5                   10                  15

Leu Pro Pro Gly Phe Arg Phe His Pro Thr Asp Glu Glu Leu Val Val
            20                  25                  30

His Tyr Leu Lys Arg Lys Ala Ala Ser Ala Pro Leu Pro Val Ala Ile
        35                  40                  45

Ile Ala Glu Val Asp Leu Tyr Lys Phe Asp Pro Trp Glu Leu Pro Ala
    50                  55                  60

Lys Ala Ser Phe Gly Glu Gln Glu Trp Tyr Phe Phe Ser Pro Arg Asp
65                  70                  75                  80

Arg Lys Tyr Pro Asn Gly Ala Arg Pro Asn Arg Ala Ala Thr Ser Gly
                85                  90                  95

```
Tyr Trp Lys Ala Thr Gly Thr Asp Lys Pro Val Leu Ala Ser Asp Gly
            100                 105                 110

Asn Gln Lys Val Gly Val Lys Lys Ala Leu Val Phe Tyr Ser Gly Lys
        115                 120                 125

Pro Pro Lys Gly Val Lys Ser Asp Trp Ile Met His Glu Tyr Arg Leu
    130                 135                 140

Ile Glu Asn Lys Pro Asn Asn Arg Pro Pro Gly Cys Asp Phe Gly Asn
145                 150                 155                 160

Lys Lys Asn Ser Leu Arg Leu Asp Asp Trp Val Leu Cys Arg Ile Tyr
                165                 170                 175

Lys Lys Asn Asn Ala Ser Arg His Val Asp Asn Asp Lys Asp His Asp
            180                 185                 190

Met Ile Asp Tyr Ile Phe Arg Lys Ile Pro Pro Ser Leu Ser Met Ala
        195                 200                 205

Ala Ala Ser Thr Gly Leu His Gln His His His Asn Val Ser Arg Ser
    210                 215                 220

Met Asn Phe Phe Pro Gly Lys Phe Ser Gly Gly Tyr Gly Ile Phe
225                 230                 235                 240

Ser Asp Gly Gly Asn Thr Ser Ile Tyr Asp Gly Gly Met Ile Asn
                245                 250                 255

Asn Ile Gly Thr Asp Ser Val Asp His Asp Asn Asn Ala Asp Val Val
            260                 265                 270

Gly Leu Asn His Ala Ser Ser Ser Gly Pro Met Met Met Ala Asn Leu
        275                 280                 285

Lys Arg Thr Leu Pro Val Pro Tyr Trp Pro Val Ala Asp Glu Glu Gln
    290                 295                 300

Asp Ala Ser Pro Ser Lys Arg Phe His Val Gly Gly Gly Gly
305                 310                 315                 320

Asp Cys Ser Asn Met Ser Ser Ser Met Met Glu Glu Thr Pro Pro Leu
                325                 330                 335

Met Gln Gln Gln Gly Gly Val Leu Gly Asp Gly Leu Phe Arg Thr Thr
            340                 345                 350

Ser Tyr Gln Leu Pro Gly Leu Asn Trp Tyr Ser Ser
        355                 360

<210> SEQ ID NO 3
<211> LENGTH: 1026
<212> TYPE: DNA
<213> ORGANISM: Arabidopsis thaliana
<220> FEATURE:
<221> NAME/KEY: CDS
<222> LOCATION: (1)..(1026)

<400> SEQUENCE: 3 atg gat aat tca gct cca gat tcg tta tcc aga tcg gaa acc gcc gtc      48
Met Asp Asn Ser Ala Pro Asp Ser Leu Ser Arg Ser Glu Thr Ala Val
1               5                   10                  15 aca tac gac tca cca tat cca ctc tac gcc atg gct ttc tct tct ctc      96
Thr Tyr Asp Ser Pro Tyr Pro Leu Tyr Ala Met Ala Phe Ser Ser Leu
            20                  25                  30 cgc tca tcc tcc ggt cac aga atc gcc gtc gga agc ttc ctc gaa gat     144
Arg Ser Ser Ser Gly His Arg Ile Ala Val Gly Ser Phe Leu Glu Asp
        35                  40                  45 tac aac aac cgc atc gac att ctc tct ttc gat tcc gat tca atg acc     192
Tyr Asn Asn Arg Ile Asp Ile Leu Ser Phe Asp Ser Asp Ser Met Thr
    50                  55                  60
```

```
gtt aag cct ctc ccg aat ctc tcc ttc gag cat cct tat cct cca aca    240
Val Lys Pro Leu Pro Asn Leu Ser Phe Glu His Pro Tyr Pro Pro Thr
 65                  70                  75                  80 aag cta atg ttc agt cct cct tct ctc cgt cgt cct tcc tcc gga gat    288
Lys Leu Met Phe Ser Pro Pro Ser Leu Arg Arg Pro Ser Ser Gly Asp
                 85                  90                  95 ctc ctc gct tcc tcc ggc gat ttc ctc cgt ctt tgg gaa att aac gaa    336
Leu Leu Ala Ser Ser Gly Asp Phe Leu Arg Leu Trp Glu Ile Asn Glu
            100                 105                 110 gat tca tca acc gtc gag cca atc tcg gtt ctc aac aac agc aaa acg    384
Asp Ser Ser Thr Val Glu Pro Ile Ser Val Leu Asn Asn Ser Lys Thr
        115                 120                 125 agc gag ttt tgt gcg ccg ttg act tcc ttc gat tgg aac gat gta gag    432
Ser Glu Phe Cys Ala Pro Leu Thr Ser Phe Asp Trp Asn Asp Val Glu
    130                 135                 140 ccg aaa cgt ctc gga act tgt agt att gat acg acg tgt acg att tgg    480
Pro Lys Arg Leu Gly Thr Cys Ser Ile Asp Thr Thr Cys Thr Ile Trp
145                 150                 155                 160 gat att gag aag tct gtt gtt gag act cag ctt ata gct cat gat aaa    528
Asp Ile Glu Lys Ser Val Val Glu Thr Gln Leu Ile Ala His Asp Lys
                165                 170                 175 gag gtt cat gac att gct tgg gga gaa gct agg gtt ttc gca tca gtc    576
Glu Val His Asp Ile Ala Trp Gly Glu Ala Arg Val Phe Ala Ser Val
            180                 185                 190 tct gct gat gga tcc gtt agg atc ttt gat tta cgt gat aag gaa cat    624
Ser Ala Asp Gly Ser Val Arg Ile Phe Asp Leu Arg Asp Lys Glu His
        195                 200                 205 tct aca atc att tac gag agt cct cag cct gat acg cct ttg tta aga    672
Ser Thr Ile Ile Tyr Glu Ser Pro Gln Pro Asp Thr Pro Leu Leu Arg
    210                 215                 220 ctt gct tgg aac aaa caa gat ctt aga tat atg gct acg att ttg atg    720
Leu Ala Trp Asn Lys Gln Asp Leu Arg Tyr Met Ala Thr Ile Leu Met
225                 230                 235                 240 gat tct aat aag gtt gtg att ctc gat att cgt tcg ccg act atg cct    768
Asp Ser Asn Lys Val Val Ile Leu Asp Ile Arg Ser Pro Thr Met Pro
                245                 250                 255 gtt gct gag ctt gaa aga cat cag gct agt gtg aat gct ata gct tgg    816
Val Ala Glu Leu Glu Arg His Gln Ala Ser Val Asn Ala Ile Ala Trp
            260                 265                 270 gcg cct cag agc tgt aaa cat att tgt tct ggt ggt gat gat aca cag    864
Ala Pro Gln Ser Cys Lys His Ile Cys Ser Gly Gly Asp Asp Thr Gln
        275                 280                 285 gct ctt att tgg gag ctt cct act gtt gct gga ccc aat ggg att gat    912
Ala Leu Ile Trp Glu Leu Pro Thr Val Ala Gly Pro Asn Gly Ile Asp
    290                 295                 300 ccg atg tcg gtt tat tcg gct ggt tcg gag att aat cag ttg cag tgg    960
Pro Met Ser Val Tyr Ser Ala Gly Ser Glu Ile Asn Gln Leu Gln Trp
305                 310                 315                 320 tct tct tcg cag cct gat tgg att ggt att gct ttt gct aac aaa atg   1008
Ser Ser Ser Gln Pro Asp Trp Ile Gly Ile Ala Phe Ala Asn Lys Met
                325                 330                 335 cag ctc ctt aga gtt tga                                            1026
Gln Leu Leu Arg Val
            340
```

<210> SEQ ID NO 4
<211> LENGTH: 341
<212> TYPE: PRT
<213> ORGANISM: Arabidopsis thaliana

<400> SEQUENCE: 4

```
Met Asp Asn Ser Ala Pro Asp Ser Leu Ser Arg Ser Glu Thr Ala Val
1               5                   10                  15

Thr Tyr Asp Ser Pro Tyr Pro Leu Tyr Ala Met Ala Phe Ser Ser Leu
            20                  25                  30

Arg Ser Ser Ser Gly His Arg Ile Ala Val Gly Ser Phe Leu Glu Asp
        35                  40                  45

Tyr Asn Asn Arg Ile Asp Ile Leu Ser Phe Asp Ser Asp Ser Met Thr
    50                  55                  60

Val Lys Pro Leu Pro Asn Leu Ser Phe Glu His Pro Tyr Pro Pro Thr
65                  70                  75                  80

Lys Leu Met Phe Ser Pro Pro Ser Leu Arg Arg Pro Ser Ser Gly Asp
                85                  90                  95

Leu Leu Ala Ser Ser Gly Asp Phe Leu Arg Leu Trp Glu Ile Asn Glu
            100                 105                 110

Asp Ser Ser Thr Val Glu Pro Ile Ser Val Leu Asn Asn Ser Lys Thr
        115                 120                 125

Ser Glu Phe Cys Ala Pro Leu Thr Ser Phe Asp Trp Asn Asp Val Glu
    130                 135                 140

Pro Lys Arg Leu Gly Thr Cys Ser Ile Asp Thr Thr Cys Thr Ile Trp
145                 150                 155                 160

Asp Ile Glu Lys Ser Val Val Glu Thr Gln Leu Ile Ala His Asp Lys
                165                 170                 175

Glu Val His Asp Ile Ala Trp Gly Glu Ala Arg Val Phe Ala Ser Val
            180                 185                 190

Ser Ala Asp Gly Ser Val Arg Ile Phe Asp Leu Arg Asp Lys Glu His
        195                 200                 205

Ser Thr Ile Ile Tyr Glu Ser Pro Gln Pro Asp Thr Pro Leu Leu Arg
    210                 215                 220

Leu Ala Trp Asn Lys Gln Asp Leu Arg Tyr Met Ala Thr Ile Leu Met
225                 230                 235                 240

Asp Ser Asn Lys Val Val Ile Leu Asp Ile Arg Ser Pro Thr Met Pro
                245                 250                 255

Val Ala Glu Leu Glu Arg His Gln Ala Ser Val Asn Ala Ile Ala Trp
            260                 265                 270

Ala Pro Gln Ser Cys Lys His Ile Cys Ser Gly Gly Asp Asp Thr Gln
        275                 280                 285

Ala Leu Ile Trp Glu Leu Pro Thr Val Ala Gly Pro Asn Gly Ile Asp
    290                 295                 300

Pro Met Ser Val Tyr Ser Ala Gly Ser Glu Ile Asn Gln Leu Gln Trp
305                 310                 315                 320

Ser Ser Ser Gln Pro Asp Trp Ile Gly Ile Ala Phe Ala Asn Lys Met
                325                 330                 335

Gln Leu Leu Arg Val
            340

<210> SEQ ID NO 5
<211> LENGTH: 825
<212> TYPE: DNA
<213> ORGANISM: Arabidopsis thaliana
<220> FEATURE:
<221> NAME/KEY: CDS
<222> LOCATION: (1)..(825)

<400> SEQUENCE: 5 atg acc cca tct cta aaa cca cta aga gag cga caa aac cat agc ttt      48
```

```
Met Thr Pro Ser Leu Lys Pro Leu Arg Glu Arg Gln Asn His Ser Phe
 1               5                  10                  15 ttt ttt gtg tcc cta ccc cat cca tgg ctg cta aaa tct tgt gat tac     96
Phe Phe Val Ser Leu Pro His Pro Trp Leu Leu Lys Ser Cys Asp Tyr
            20                  25                  30 ctt ctt gtc tcc ttc ctc ttc tct ttc cct ctt tta tat aag aac caa    144
Leu Leu Val Ser Phe Leu Phe Ser Phe Pro Leu Leu Tyr Lys Asn Gln
             35                  40                  45 aac atc cac agc ttt tgt tcc atc atc act tgc aga ttc ttt ctc tct    192
Asn Ile His Ser Phe Cys Ser Ile Ile Thr Cys Arg Phe Phe Leu Ser
 50                  55                  60 ttc gta aaa atg gcg agt ttt gag gaa agc tct gat ttg gaa gct ata    240
Phe Val Lys Met Ala Ser Phe Glu Glu Ser Ser Asp Leu Glu Ala Ile
65                  70                  75                  80 cag agc cat ctc tta gaa gac ttg ttg gtt tgt gat ggt ttc atg gga    288
Gln Ser His Leu Leu Glu Asp Leu Leu Val Cys Asp Gly Phe Met Gly
                 85                  90                  95 gat ttt gac ttc gat gct tct ttt gtc tca gga ctt tgg tgt ata gaa    336
Asp Phe Asp Phe Asp Ala Ser Phe Val Ser Gly Leu Trp Cys Ile Glu
            100                 105                 110 cca cac gtt cct aaa caa gaa cct gat tct cca gtt ctt gat ccg gat    384
Pro His Val Pro Lys Gln Glu Pro Asp Ser Pro Val Leu Asp Pro Asp
            115                 120                 125 tct ttc gtc aac gag ttc ttg caa gtg gaa ggg gaa tca tca tca tca    432
Ser Phe Val Asn Glu Phe Leu Gln Val Glu Gly Glu Ser Ser Ser Ser
        130                 135                 140 tca tca cca gag ctg aat tca tcg tca tca aca tat gag act gat cag    480
Ser Ser Pro Glu Leu Asn Ser Ser Ser Ser Thr Tyr Glu Thr Asp Gln
145                 150                 155                 160 agt gtg aaa aag gca gag agg ttc gaa gaa gaa gta gat gct aga cat    528
Ser Val Lys Lys Ala Glu Arg Phe Glu Glu Glu Val Asp Ala Arg His
                165                 170                 175 tac cga gga gtg agg cga agg ccg tgg ggg aaa ttt gca gca gag att    576
Tyr Arg Gly Val Arg Arg Arg Pro Trp Gly Lys Phe Ala Ala Glu Ile
            180                 185                 190 cga gat cca gca aag aaa gga tca aga atc tgg cta gga aca ttt gag    624
Arg Asp Pro Ala Lys Lys Gly Ser Arg Ile Trp Leu Gly Thr Phe Glu
            195                 200                 205 agt gat gtt gat gct gca aga gcc tat gac tgt gca gct ttc aag ctc    672
Ser Asp Val Asp Ala Ala Arg Ala Tyr Asp Cys Ala Ala Phe Lys Leu
210                 215                 220 cgg gga aga aaa gcc gtg ctc aac ttc cct ctt gac gcc ggg aaa tat    720
Arg Gly Arg Lys Ala Val Leu Asn Phe Pro Leu Asp Ala Gly Lys Tyr
225                 230                 235                 240 gaa gct cca gcg aat tca gga agg aaa agg aag aga agt gat gtg cat    768
Glu Ala Pro Ala Asn Ser Gly Arg Lys Arg Lys Arg Ser Asp Val His
                245                 250                 255 gaa gag ctt caa aga act cag agc aat tca tct tca tct tcc tgt gat    816
Glu Glu Leu Gln Arg Thr Gln Ser Asn Ser Ser Ser Ser Ser Cys Asp
            260                 265                 270 gca ttt tag                                                        825
Ala Phe

<210> SEQ ID NO 6
<211> LENGTH: 274
<212> TYPE: PRT
<213> ORGANISM: Arabidopsis thaliana

<400> SEQUENCE: 6

Met Thr Pro Ser Leu Lys Pro Leu Arg Glu Arg Gln Asn His Ser Phe
```

-continued

```
 1               5                   10                  15
Phe Phe Val Ser Leu Pro His Pro Trp Leu Lys Ser Cys Asp Tyr
                20                  25                  30
Leu Leu Val Ser Phe Leu Phe Ser Phe Pro Leu Leu Tyr Lys Asn Gln
                35                  40                  45
Asn Ile His Ser Phe Cys Ser Ile Ile Thr Cys Arg Phe Phe Leu Ser
 50                  55                  60
Phe Val Lys Met Ala Ser Phe Glu Glu Ser Ser Asp Leu Glu Ala Ile
 65                  70                  75                  80
Gln Ser His Leu Leu Glu Asp Leu Leu Val Cys Asp Gly Phe Met Gly
                85                  90                  95
Asp Phe Asp Phe Asp Ala Ser Phe Val Ser Gly Leu Trp Cys Ile Glu
                100                 105                 110
Pro His Val Pro Lys Gln Glu Pro Asp Ser Pro Val Leu Asp Pro Asp
                115                 120                 125
Ser Phe Val Asn Glu Phe Leu Gln Val Glu Gly Glu Ser Ser Ser Ser
 130                 135                 140
Ser Ser Pro Glu Leu Asn Ser Ser Ser Thr Tyr Glu Thr Asp Gln
 145                 150                 155                 160
Ser Val Lys Lys Ala Glu Arg Phe Glu Glu Val Asp Ala Arg His
                165                 170                 175
Tyr Arg Gly Val Arg Arg Pro Trp Gly Lys Phe Ala Ala Glu Ile
                180                 185                 190
Arg Asp Pro Ala Lys Lys Gly Ser Arg Ile Trp Leu Gly Thr Phe Glu
                195                 200                 205
Ser Asp Val Asp Ala Ala Arg Ala Tyr Asp Cys Ala Ala Phe Lys Leu
 210                 215                 220
Arg Gly Arg Lys Ala Val Leu Asn Phe Pro Leu Asp Ala Gly Lys Tyr
 225                 230                 235                 240
Glu Ala Pro Ala Asn Ser Gly Arg Lys Arg Lys Arg Ser Asp Val His
                245                 250                 255
Glu Glu Leu Gln Arg Thr Gln Ser Asn Ser Ser Ser Ser Cys Asp
                260                 265                 270
Ala Phe

<210> SEQ ID NO 7
<211> LENGTH: 588
<212> TYPE: DNA
<213> ORGANISM: Arabidopsis thaliana
<220> FEATURE:
<221> NAME/KEY: CDS
<222> LOCATION: (1)..(588)

<400> SEQUENCE: 7 atg gtg aag caa gcg atg aag gaa gag gag aag aag aga aac acg gcg     48
Met Val Lys Gln Ala Met Lys Glu Glu Glu Lys Lys Arg Asn Thr Ala
 1               5                  10                  15 atg cag tca aag tac aaa gga gtg agg aag agg aaa tgg gga aaa tgg     96
Met Gln Ser Lys Tyr Lys Gly Val Arg Lys Arg Lys Trp Gly Lys Trp
                20                  25                  30 gta tcg gag atc aga ctt cca cac agc aga gaa cga att tgg tta ggc    144
Val Ser Glu Ile Arg Leu Pro His Ser Arg Glu Arg Ile Trp Leu Gly
                35                  40                  45 tct tac gac act ccc gag aag gcg gcg cgt gct ttc gac gcc gct caa    192
Ser Tyr Asp Thr Pro Glu Lys Ala Ala Arg Ala Phe Asp Ala Ala Gln
 50                  55                  60
```

```
ttt tgt ctc cgc ggc ggc gat gct aat ttc aat ttc cct aat aat cca      240
Phe Cys Leu Arg Gly Gly Asp Ala Asn Phe Asn Phe Pro Asn Asn Pro
 65                  70                  75                  80 ccg tcg atc tcc gta gaa aag tcg ttg acg cct ccg gag att cag gaa      288
Pro Ser Ile Ser Val Glu Lys Ser Leu Thr Pro Pro Glu Ile Gln Glu
                 85                  90                  95 gct gct gct aga ttc gct aac aca ttc caa gac att gtc aag gga gaa      336
Ala Ala Ala Arg Phe Ala Asn Thr Phe Gln Asp Ile Val Lys Gly Glu
            100                 105                 110 gaa gaa tcg ggt tta gta ccc gga tcc gag atc cga cca gag tct cct      384
Glu Glu Ser Gly Leu Val Pro Gly Ser Glu Ile Arg Pro Glu Ser Pro
        115                 120                 125 tct aca tct gca tct gtt gct aca tcg acg gtg gat tat gat ttt tcg      432
Ser Thr Ser Ala Ser Val Ala Thr Ser Thr Val Asp Tyr Asp Phe Ser
    130                 135                 140 ttt ttg gat ttg ctt ccg atg aat ttc ggg ttt gat tcc ttc tcc gac      480
Phe Leu Asp Leu Leu Pro Met Asn Phe Gly Phe Asp Ser Phe Ser Asp
145                 150                 155                 160 gac ttc tct ggc ttc tcc ggt ggt gat cga ttt aca gag att tta ccc      528
Asp Phe Ser Gly Phe Ser Gly Gly Asp Arg Phe Thr Glu Ile Leu Pro
                165                 170                 175 atc gaa gat tac gga gga gag agt tta tta gat gaa tct ttg att ctt      576
Ile Glu Asp Tyr Gly Gly Glu Ser Leu Leu Asp Glu Ser Leu Ile Leu
            180                 185                 190 tgg gat ttt tga                                                      588
Trp Asp Phe
        195

<210> SEQ ID NO 8
<211> LENGTH: 195
<212> TYPE: PRT
<213> ORGANISM: Arabidopsis thaliana

<400> SEQUENCE: 8

Met Val Lys Gln Ala Met Lys Glu Glu Lys Lys Arg Asn Thr Ala
  1               5                  10                  15

Met Gln Ser Lys Tyr Lys Gly Val Arg Lys Arg Lys Trp Gly Lys Trp
                 20                  25                  30

Val Ser Glu Ile Arg Leu Pro His Ser Arg Glu Arg Ile Trp Leu Gly
             35                  40                  45

Ser Tyr Asp Thr Pro Glu Lys Ala Ala Arg Ala Phe Asp Ala Ala Gln
 50                  55                  60

Phe Cys Leu Arg Gly Gly Asp Ala Asn Phe Asn Phe Pro Asn Asn Pro
 65                  70                  75                  80

Pro Ser Ile Ser Val Glu Lys Ser Leu Thr Pro Pro Glu Ile Gln Glu
                 85                  90                  95

Ala Ala Ala Arg Phe Ala Asn Thr Phe Gln Asp Ile Val Lys Gly Glu
            100                 105                 110

Glu Glu Ser Gly Leu Val Pro Gly Ser Glu Ile Arg Pro Glu Ser Pro
        115                 120                 125

Ser Thr Ser Ala Ser Val Ala Thr Ser Thr Val Asp Tyr Asp Phe Ser
    130                 135                 140

Phe Leu Asp Leu Leu Pro Met Asn Phe Gly Phe Asp Ser Phe Ser Asp
145                 150                 155                 160

Asp Phe Ser Gly Phe Ser Gly Gly Asp Arg Phe Thr Glu Ile Leu Pro
                165                 170                 175

Ile Glu Asp Tyr Gly Gly Glu Ser Leu Leu Asp Glu Ser Leu Ile Leu
            180                 185                 190
```

Trp Asp Phe
    195

<210> SEQ ID NO 9
<211> LENGTH: 1098
<212> TYPE: DNA
<213> ORGANISM: Arabidopsis thaliana
<220> FEATURE:
<221> NAME/KEY: CDS
<222> LOCATION: (1)..(1098)

<400> SEQUENCE: 9

| | | | | | | | | | | | | | | | | |
|---|---|---|---|---|---|---|---|---|---|---|---|---|---|---|---|---|
| atg | act | cgt | cga | tgt | tct | cac | tgc | aat | cac | aat | ggc | cac | aac | tct | cgg | 48 |
| Met | Thr | Arg | Arg | Cys | Ser | His | Cys | Asn | His | Asn | Gly | His | Asn | Ser | Arg | |
| 1 | | | | 5 | | | | | 10 | | | | | 15 | | |

| act | tgt | ccc | aat | cgc | ggc | gtg | aag | ctc | ttt | ggt | gtt | cgg | ctc | acc | gaa | 96 |
|---|---|---|---|---|---|---|---|---|---|---|---|---|---|---|---|---|
| Thr | Cys | Pro | Asn | Arg | Gly | Val | Lys | Leu | Phe | Gly | Val | Arg | Leu | Thr | Glu | |
| | | | 20 | | | | | 25 | | | | | 30 | | | |

| ggt | tcg | atc | cgg | aaa | agt | gca | agt | atg | ggt | aat | ctt | agc | cat | tac | acg | 144 |
|---|---|---|---|---|---|---|---|---|---|---|---|---|---|---|---|---|
| Gly | Ser | Ile | Arg | Lys | Ser | Ala | Ser | Met | Gly | Asn | Leu | Ser | His | Tyr | Thr | |
| | | 35 | | | | | 40 | | | | | 45 | | | | |

| ggt | tct | gga | tcg | ggt | ggg | cat | gga | acc | ggg | tcc | aac | act | ccg | ggt | tct | 192 |
|---|---|---|---|---|---|---|---|---|---|---|---|---|---|---|---|---|
| Gly | Ser | Gly | Ser | Gly | Gly | His | Gly | Thr | Gly | Ser | Asn | Thr | Pro | Gly | Ser | |
| 50 | | | | | 55 | | | | | 60 | | | | | | |

| ccg | ggt | gat | gtc | cct | gac | cat | gtc | gct | ggt | gat | ggt | tac | gct | tct | gag | 240 |
|---|---|---|---|---|---|---|---|---|---|---|---|---|---|---|---|---|
| Pro | Gly | Asp | Val | Pro | Asp | His | Val | Ala | Gly | Asp | Gly | Tyr | Ala | Ser | Glu | |
| 65 | | | | 70 | | | | | 75 | | | | | 80 | | |

| gat | ttc | gtt | gct | ggc | tct | tcc | tct | agc | cgc | gag | aga | aag | aaa | gga | act | 288 |
|---|---|---|---|---|---|---|---|---|---|---|---|---|---|---|---|---|
| Asp | Phe | Val | Ala | Gly | Ser | Ser | Ser | Ser | Arg | Glu | Arg | Lys | Lys | Gly | Thr | |
| | | | | 85 | | | | | 90 | | | | | 95 | | |

| cca | tgg | aca | gag | gaa | gaa | cac | agg | atg | ttc | tta | tta | ggt | tta | cag | aag | 336 |
|---|---|---|---|---|---|---|---|---|---|---|---|---|---|---|---|---|
| Pro | Trp | Thr | Glu | Glu | Glu | His | Arg | Met | Phe | Leu | Leu | Gly | Leu | Gln | Lys | |
| | | | 100 | | | | | 105 | | | | | 110 | | | |

| ctg | ggt | aaa | ggt | gat | tgg | aga | ggt | atc | tca | aga | aac | tat | gtg | acc | act | 384 |
|---|---|---|---|---|---|---|---|---|---|---|---|---|---|---|---|---|
| Leu | Gly | Lys | Gly | Asp | Trp | Arg | Gly | Ile | Ser | Arg | Asn | Tyr | Val | Thr | Thr | |
| | | 115 | | | | | 120 | | | | | 125 | | | | |

| agg | aca | cct | aca | caa | gtt | gct | agc | cat | gct | cag | aag | tat | ttc | atc | aga | 432 |
|---|---|---|---|---|---|---|---|---|---|---|---|---|---|---|---|---|
| Arg | Thr | Pro | Thr | Gln | Val | Ala | Ser | His | Ala | Gln | Lys | Tyr | Phe | Ile | Arg | |
| 130 | | | | | 135 | | | | | 140 | | | | | | |

| caa | tcc | aat | gtc | tct | cgt | cgc | aaa | aga | cgt | tct | agt | ctc | ttt | gat | atg | 480 |
|---|---|---|---|---|---|---|---|---|---|---|---|---|---|---|---|---|
| Gln | Ser | Asn | Val | Ser | Arg | Arg | Lys | Arg | Arg | Ser | Ser | Leu | Phe | Asp | Met | |
| 145 | | | | | 150 | | | | | 155 | | | | | 160 | |

| gtt | cct | gat | gag | gtt | gga | gat | att | ccc | atg | gat | ttg | caa | gaa | cca | gag | 528 |
|---|---|---|---|---|---|---|---|---|---|---|---|---|---|---|---|---|
| Val | Pro | Asp | Glu | Val | Gly | Asp | Ile | Pro | Met | Asp | Leu | Gln | Glu | Pro | Glu | |
| | | | | 165 | | | | | 170 | | | | | 175 | | |

| gaa | gat | aat | att | cct | gtg | gaa | act | gaa | atg | caa | ggt | gct | gac | tct | att | 576 |
|---|---|---|---|---|---|---|---|---|---|---|---|---|---|---|---|---|
| Glu | Asp | Asn | Ile | Pro | Val | Glu | Thr | Glu | Met | Gln | Gly | Ala | Asp | Ser | Ile | |
| | | | 180 | | | | | 185 | | | | | 190 | | | |

| cat | cag | aca | ctt | gct | cct | agc | tca | ctt | cac | gca | ccg | tca | atc | ttg | gaa | 624 |
|---|---|---|---|---|---|---|---|---|---|---|---|---|---|---|---|---|
| His | Gln | Thr | Leu | Ala | Pro | Ser | Ser | Leu | His | Ala | Pro | Ser | Ile | Leu | Glu | |
| | | 195 | | | | | 200 | | | | | 205 | | | | |

| atc | gaa | gaa | tgt | gaa | tca | atg | gac | tcc | aca | aac | tct | acc | acc | ggg | gaa | 672 |
|---|---|---|---|---|---|---|---|---|---|---|---|---|---|---|---|---|
| Ile | Glu | Glu | Cys | Glu | Ser | Met | Asp | Ser | Thr | Asn | Ser | Thr | Thr | Gly | Glu | |
| | 210 | | | | | 215 | | | | | 220 | | | | | |

| cca | acc | gca | act | gcc | gct | gct | gct | tct | tct | tct | tcc | aga | cta | gaa | gaa | 720 |
|---|---|---|---|---|---|---|---|---|---|---|---|---|---|---|---|---|
| Pro | Thr | Ala | Thr | Ala | Ala | Ala | Ala | Ser | Ser | Ser | Ser | Arg | Leu | Glu | Glu | |
| 225 | | | | | 230 | | | | | 235 | | | | | 240 | |

| acc | aca | caa | ctg | caa | tca | caa | ctg | caa | ccg | cag | ccg | caa | cta | cct | ggc | 768 |
|---|---|---|---|---|---|---|---|---|---|---|---|---|---|---|---|---|
| Thr | Thr | Gln | Leu | Gln | Ser | Gln | Leu | Gln | Pro | Gln | Pro | Gln | Leu | Pro | Gly | |
| | | | | 245 | | | | | 250 | | | | | 255 | | |

```
tca ttc ccc ata cta tat ccg acc tac ttt tca cca tat tac ccg ttt       816
Ser Phe Pro Ile Leu Tyr Pro Thr Tyr Phe Ser Pro Tyr Tyr Pro Phe
        260                 265                 270 cca ttc cca ata tgg cct gct ggt tat gtt cct gaa cca ccc aag aaa       864
Pro Phe Pro Ile Trp Pro Ala Gly Tyr Val Pro Glu Pro Pro Lys Lys
        275                 280                 285 gag gaa act cat gaa att ctc aga cca act gct gtg cac tcg aaa gct       912
Glu Glu Thr His Glu Ile Leu Arg Pro Thr Ala Val His Ser Lys Ala
    290                 295                 300 cct atc aat gtt gac gag ctt ctt ggt atg tct aag ctc agc ctt gca       960
Pro Ile Asn Val Asp Glu Leu Leu Gly Met Ser Lys Leu Ser Leu Ala
305                 310                 315                 320 gag tcc aac aaa cat gga gaa tcc gat cag tct ctt tca ttg aag cta      1008
Glu Ser Asn Lys His Gly Glu Ser Asp Gln Ser Leu Ser Leu Lys Leu
                325                 330                 335 ggt ggc ggg tca tct tca aga caa tca gca ttt cac ccg aat cct agc      1056
Gly Gly Gly Ser Ser Ser Arg Gln Ser Ala Phe His Pro Asn Pro Ser
                340                 345                 350 tct gat agt tca gac atc aaa agc gtg ata cac gct tta taa             1098
Ser Asp Ser Ser Asp Ile Lys Ser Val Ile His Ala Leu
        355                 360                 365

<210> SEQ ID NO 10
<211> LENGTH: 365
<212> TYPE: PRT
<213> ORGANISM: Arabidopsis thaliana

<400> SEQUENCE: 10

Met Thr Arg Arg Cys Ser His Cys Asn His Asn Gly His Asn Ser Arg
1               5                   10                  15

Thr Cys Pro Asn Arg Gly Val Lys Leu Phe Gly Val Arg Leu Thr Glu
            20                  25                  30

Gly Ser Ile Arg Lys Ser Ala Ser Met Gly Asn Leu Ser His Tyr Thr
        35                  40                  45

Gly Ser Gly Ser Gly Gly His Gly Thr Gly Ser Asn Thr Pro Gly Ser
    50                  55                  60

Pro Gly Asp Val Pro Asp His Val Ala Gly Asp Gly Tyr Ala Ser Glu
65                  70                  75                  80

Asp Phe Val Ala Gly Ser Ser Ser Arg Glu Arg Lys Lys Gly Thr
                85                  90                  95

Pro Trp Thr Glu Glu His Arg Met Phe Leu Leu Gly Leu Gln Lys
            100                 105                 110

Leu Gly Lys Gly Asp Trp Arg Gly Ile Ser Arg Asn Tyr Val Thr Thr
        115                 120                 125

Arg Thr Pro Thr Gln Val Ala Ser His Ala Gln Lys Tyr Phe Ile Arg
    130                 135                 140

Gln Ser Asn Val Ser Arg Arg Lys Arg Arg Ser Ser Leu Phe Asp Met
145                 150                 155                 160

Val Pro Asp Glu Val Gly Asp Ile Pro Met Asp Leu Gln Glu Pro Glu
                165                 170                 175

Glu Asp Asn Ile Pro Val Glu Thr Glu Met Gln Gly Ala Asp Ser Ile
            180                 185                 190

His Gln Thr Leu Ala Pro Ser Leu His Ala Pro Ser Ile Leu Glu
        195                 200                 205

Ile Glu Glu Cys Glu Ser Met Asp Ser Thr Asn Ser Thr Thr Gly Glu
    210                 215                 220

Pro Thr Ala Thr Ala Ala Ala Ala Ser Ser Ser Ser Arg Leu Glu Glu
```

-continued

```
                225                 230                 235                 240
            Thr Thr Gln Leu Gln Ser Gln Leu Gln Pro Gln Pro Gln Leu Pro Gly
                            245                 250                 255

Ser Phe Pro Ile Leu Tyr Pro Thr Tyr Phe Ser Pro Tyr Tyr Pro Phe
                            260                 265                 270

Pro Phe Pro Ile Trp Pro Ala Gly Tyr Val Pro Glu Pro Lys Lys
                            275                 280                 285

Glu Glu Thr His Glu Ile Leu Arg Pro Thr Ala Val His Ser Lys Ala
                            290                 295                 300

Pro Ile Asn Val Asp Glu Leu Leu Gly Met Ser Lys Leu Ser Leu Ala
            305                 310                 315                 320

Glu Ser Asn Lys His Gly Glu Ser Asp Gln Ser Leu Ser Leu Lys Leu
                            325                 330                 335

Gly Gly Gly Ser Ser Ser Arg Gln Ser Ala Phe His Pro Asn Pro Ser
                            340                 345                 350

Ser Asp Ser Ser Asp Ile Lys Ser Val Ile His Ala Leu
                            355                 360                 365

<210> SEQ ID NO 11
<211> LENGTH: 546
<212> TYPE: DNA
<213> ORGANISM: Arabidopsis thaliana
<220> FEATURE:
<221> NAME/KEY: CDS
<222> LOCATION: (1)..(546)

<400> SEQUENCE: 11 atg gca cga cca caa caa cgc ttt cga ggc gtt aga cag agg cat tgg      48
Met Ala Arg Pro Gln Gln Arg Phe Arg Gly Val Arg Gln Arg His Trp
1               5                  10                  15 ggc tct tgg gtc tcc gaa att cgt cac cct ctc ttg aaa aca aga atc      96
Gly Ser Trp Val Ser Glu Ile Arg His Pro Leu Leu Lys Thr Arg Ile
                20                  25                  30 tgg cta ggg acg ttt gag aca gcg gag gat gca gca agg gcc tac gac     144
Trp Leu Gly Thr Phe Glu Thr Ala Glu Asp Ala Ala Arg Ala Tyr Asp
            35                  40                  45 gag gcg gct agg cta atg tgt ggc ccg aga gct cgt act aat ttc cca     192
Glu Ala Ala Arg Leu Met Cys Gly Pro Arg Ala Arg Thr Asn Phe Pro
        50                  55                  60 tac aac cct aat gcc att cct act tcc tct tcc aag ctt cta tca gca     240
Tyr Asn Pro Asn Ala Ile Pro Thr Ser Ser Ser Lys Leu Leu Ser Ala
65                  70                  75                  80 act ctt acc gct aaa ctc cac aaa tgc tac atg gct tct ctt caa atg     288
Thr Leu Thr Ala Lys Leu His Lys Cys Tyr Met Ala Ser Leu Gln Met
                85                  90                  95 acc aag caa acg caa aca caa acg caa acg cag acc gca aga tca caa     336
Thr Lys Gln Thr Gln Thr Gln Thr Gln Thr Gln Thr Ala Arg Ser Gln
                100                 105                 110 tcc gcg gac agt gac ggt gtg acg gct aac gaa agt cat ttg aac aga     384
Ser Ala Asp Ser Asp Gly Val Thr Ala Asn Glu Ser His Leu Asn Arg
            115                 120                 125 gga gta acg gag acg aca gag atc aag tgg gaa gat gga aat gcg aat     432
Gly Val Thr Glu Thr Thr Glu Ile Lys Trp Glu Asp Gly Asn Ala Asn
        130                 135                 140 atg caa cag aat ttt agg cca ttg gag gaa gat cat atc gag caa atg     480
Met Gln Gln Asn Phe Arg Pro Leu Glu Glu Asp His Ile Glu Gln Met
145                 150                 155                 160 att gag gag ctg ctt cac tac ggt tcc att gag ctt tgc tct gtt tta     528
Ile Glu Glu Leu Leu His Tyr Gly Ser Ile Glu Leu Cys Ser Val Leu
```

```
                        165                 170                 175
cca act cag acg ctg tga                                                     546
Pro Thr Gln Thr Leu
            180

<210> SEQ ID NO 12
<211> LENGTH: 181
<212> TYPE: PRT
<213> ORGANISM: Arabidopsis thaliana

<400> SEQUENCE: 12

Met Ala Arg Pro Gln Gln Arg Phe Arg Gly Val Arg Gln Arg His Trp
1               5                   10                  15

Gly Ser Trp Val Ser Glu Ile Arg His Pro Leu Leu Lys Thr Arg Ile
            20                  25                  30

Trp Leu Gly Thr Phe Glu Thr Ala Glu Asp Ala Ala Arg Ala Tyr Asp
        35                  40                  45

Glu Ala Ala Arg Leu Met Cys Gly Pro Arg Ala Arg Thr Asn Phe Pro
    50                  55                  60

Tyr Asn Pro Asn Ala Ile Pro Thr Ser Ser Lys Leu Leu Ser Ala
65                  70                  75                  80

Thr Leu Thr Ala Lys Leu His Lys Cys Tyr Met Ala Ser Leu Gln Met
                85                  90                  95

Thr Lys Gln Thr Gln Thr Gln Thr Gln Thr Ala Arg Ser Gln
                100                 105                 110

Ser Ala Asp Ser Asp Gly Val Thr Ala Asn Glu Ser His Leu Asn Arg
            115                 120                 125

Gly Val Thr Glu Thr Thr Glu Ile Lys Trp Glu Asp Gly Asn Ala Asn
        130                 135                 140

Met Gln Gln Asn Phe Arg Pro Leu Glu Glu Asp His Ile Glu Gln Met
145                 150                 155                 160

Ile Glu Glu Leu Leu His Tyr Gly Ser Ile Glu Leu Cys Ser Val Leu
                165                 170                 175

Pro Thr Gln Thr Leu
            180

<210> SEQ ID NO 13
<211> LENGTH: 1005
<212> TYPE: DNA
<213> ORGANISM: Arabidopsis thaliana
<220> FEATURE:
<221> NAME/KEY: CDS
<222> LOCATION: (1)..(1005)

<400> SEQUENCE: 13 atg aac ata tca gta aac gga cag tca caa gta cct cct ggc ttt agg     48
Met Asn Ile Ser Val Asn Gly Gln Ser Gln Val Pro Pro Gly Phe Arg
1               5                   10                  15 ttt cac cca acc gag gaa gag ctc ttg aag tat tac ctc cgc aag aaa     96
Phe His Pro Thr Glu Glu Glu Leu Leu Lys Tyr Tyr Leu Arg Lys Lys
            20                  25                  30 atc tct aac atc aag atc gat ctc gat gtt att cct gac att gat ctc    144
Ile Ser Asn Ile Lys Ile Asp Leu Asp Val Ile Pro Asp Ile Asp Leu
        35                  40                  45 aac aag ctc gag cct tgg gat att caa gag atg tgt aag att gga acg    192
Asn Lys Leu Glu Pro Trp Asp Ile Gln Glu Met Cys Lys Ile Gly Thr
    50                  55                  60 acg ccg caa aac gat tgg tac ttt tat agc cat aag gac aag aag tat    240
Thr Pro Gln Asn Asp Trp Tyr Phe Tyr Ser His Lys Asp Lys Lys Tyr
```

```
                65                  70                  75                  80
ccc acc ggg act aga acc aac aga gcc acc acg gtc gga ttt tgg aaa         288
Pro Thr Gly Thr Arg Thr Asn Arg Ala Thr Thr Val Gly Phe Trp Lys
                    85                  90                  95 gcg acg gga cgt gac aag acc ata tat acc aat ggt gat aga atc ggg         336
Ala Thr Gly Arg Asp Lys Thr Ile Tyr Thr Asn Gly Asp Arg Ile Gly
                100                 105                 110 atg cga aag acg ctt gtc ttc tac aaa ggt cga gcc cct cat ggt cag         384
Met Arg Lys Thr Leu Val Phe Tyr Lys Gly Arg Ala Pro His Gly Gln
            115                 120                 125 aaa tcc gat tgg atc atg cac gaa tat aga ctc gac gag agt gta tta         432
Lys Ser Asp Trp Ile Met His Glu Tyr Arg Leu Asp Glu Ser Val Leu
        130                 135                 140 atc tcc tcg tgt ggc gat cat gac gtc aac gta gaa acg tgt gat gtc         480
Ile Ser Ser Cys Gly Asp His Asp Val Asn Val Glu Thr Cys Asp Val
145                 150                 155                 160 ata gga agt gac gaa gga tgg gtg gtg tgt cgt gtt ttc aag aaa aat         528
Ile Gly Ser Asp Glu Gly Trp Val Val Cys Arg Val Phe Lys Lys Asn
                165                 170                 175 aac ctt tgc aaa aac atg att agt agt agc ccg gcg agt tcg gtg aaa         576
Asn Leu Cys Lys Asn Met Ile Ser Ser Ser Pro Ala Ser Ser Val Lys
                180                 185                 190 acg ccg tcg ttc aat gag gag act atc gag caa ctt ctc gaa gtt atg         624
Thr Pro Ser Phe Asn Glu Glu Thr Ile Glu Gln Leu Leu Glu Val Met
            195                 200                 205 ggg caa tct tgt aaa gga gag ata gtt tta gac cct ttc tta aaa ctc         672
Gly Gln Ser Cys Lys Gly Glu Ile Val Leu Asp Pro Phe Leu Lys Leu
        210                 215                 220 cct aac ctc gaa tgc cat aac aac acc acc atc acg agt tat cag tgg         720
Pro Asn Leu Glu Cys His Asn Asn Thr Thr Ile Thr Ser Tyr Gln Trp
225                 230                 235                 240 tta atc gac gac caa gtc aac aac tgc cac gtc agc aaa gtt atg gat         768
Leu Ile Asp Asp Gln Val Asn Asn Cys His Val Ser Lys Val Met Asp
                245                 250                 255 ccc agc ttc atc act agc tgg gcc gct ttg gat cgg ctc gtt gcc tca         816
Pro Ser Phe Ile Thr Ser Trp Ala Ala Leu Asp Arg Leu Val Ala Ser
                260                 265                 270 cag tta aat ggg ccc aac tcg tat tca ata cca gcc gtt aat gag act         864
Gln Leu Asn Gly Pro Asn Ser Tyr Ser Ile Pro Ala Val Asn Glu Thr
            275                 280                 285 tca caa tca ccg tat cat gga ctg aac cgg tcc ggt tgt aat acc ggt         912
Ser Gln Ser Pro Tyr His Gly Leu Asn Arg Ser Gly Cys Asn Thr Gly
        290                 295                 300 tta aca cca gat tac tat ata ccg gag att gat tta tgg aac gag gca         960
Leu Thr Pro Asp Tyr Tyr Ile Pro Glu Ile Asp Leu Trp Asn Glu Ala
305                 310                 315                 320 gat ttc gcg aga acg aca tgc cac ttg ttg aac ggt agt gga taa             1005
Asp Phe Ala Arg Thr Thr Cys His Leu Leu Asn Gly Ser Gly
                325                 330

<210> SEQ ID NO 14
<211> LENGTH: 334
<212> TYPE: PRT
<213> ORGANISM: Arabidopsis thaliana

<400> SEQUENCE: 14

Met Asn Ile Ser Val Asn Gly Gln Ser Gln Val Pro Pro Gly Phe Arg
1               5                   10                  15

Phe His Pro Thr Glu Glu Glu Leu Leu Lys Tyr Tyr Leu Arg Lys Lys
            20                  25                  30
```

Ile Ser Asn Ile Lys Ile Asp Leu Asp Val Ile Pro Asp Ile Asp Leu
            35                  40                  45

Asn Lys Leu Glu Pro Trp Asp Ile Gln Glu Met Cys Lys Ile Gly Thr
 50                  55                  60

Thr Pro Gln Asn Asp Trp Tyr Phe Tyr Ser His Lys Asp Lys Lys Tyr
 65                  70                  75                  80

Pro Thr Gly Thr Arg Thr Asn Arg Ala Thr Thr Val Gly Phe Trp Lys
                 85                  90                  95

Ala Thr Gly Arg Asp Lys Thr Ile Tyr Thr Asn Gly Asp Arg Ile Gly
                100                 105                 110

Met Arg Lys Thr Leu Val Phe Tyr Lys Gly Arg Ala Pro His Gly Gln
            115                 120                 125

Lys Ser Asp Trp Ile Met His Glu Tyr Arg Leu Asp Glu Ser Val Leu
130                 135                 140

Ile Ser Ser Cys Gly Asp His Asp Val Asn Val Glu Thr Cys Asp Val
145                 150                 155                 160

Ile Gly Ser Asp Glu Gly Trp Val Val Cys Arg Val Phe Lys Lys Asn
                165                 170                 175

Asn Leu Cys Lys Asn Met Ile Ser Ser Ser Pro Ala Ser Ser Val Lys
            180                 185                 190

Thr Pro Ser Phe Asn Glu Glu Thr Ile Glu Gln Leu Leu Glu Val Met
            195                 200                 205

Gly Gln Ser Cys Lys Gly Glu Ile Val Leu Asp Pro Phe Leu Lys Leu
210                 215                 220

Pro Asn Leu Glu Cys His Asn Asn Thr Thr Ile Thr Ser Tyr Gln Trp
225                 230                 235                 240

Leu Ile Asp Asp Gln Val Asn Asn Cys His Val Ser Lys Val Met Asp
                245                 250                 255

Pro Ser Phe Ile Thr Ser Trp Ala Ala Leu Asp Arg Leu Val Ala Ser
            260                 265                 270

Gln Leu Asn Gly Pro Asn Ser Tyr Ser Ile Pro Ala Val Asn Glu Thr
            275                 280                 285

Ser Gln Ser Pro Tyr His Gly Leu Asn Arg Ser Gly Cys Asn Thr Gly
290                 295                 300

Leu Thr Pro Asp Tyr Tyr Ile Pro Glu Ile Asp Leu Trp Asn Glu Ala
305                 310                 315                 320

Asp Phe Ala Arg Thr Thr Cys His Leu Leu Asn Gly Ser Gly
                325                 330

<210> SEQ ID NO 15
<211> LENGTH: 30
<212> TYPE: DNA
<213> ORGANISM: Artificial Sequence
<220> FEATURE:
<223> OTHER INFORMATION: Synthetic DNA for a forward primer of At3g15510

<400> SEQUENCE: 15
gatggagagc accgattctt ccggtggtcc                                     30

<210> SEQ ID NO 16
<211> LENGTH: 29
<212> TYPE: DNA
<213> ORGANISM: Artificial Sequence
<220> FEATURE:
<223> OTHER INFORMATION: Synthetic DNA for a reverse primer of At3g15510

<400> SEQUENCE: 16

-continued agaagagtac caatttaaac cgggtaatt         29

<210> SEQ ID NO 17
<211> LENGTH: 30
<212> TYPE: DNA
<213> ORGANISM: Artificial Sequence
<220> FEATURE:
<223> OTHER INFORMATION: Synthetic DNA for a forward primer of At5g24520

<400> SEQUENCE: 17
gatggataat tcagctccag attcgttatc         30

<210> SEQ ID NO 18
<211> LENGTH: 30
<212> TYPE: DNA
<213> ORGANISM: Artificial Sequence
<220> FEATURE:
<223> OTHER INFORMATION: Synthetic DNA for a reverse primer of At5g24520

<400> SEQUENCE: 18
aactctaagg agctgcattt tgttagcaaa         30

<210> SEQ ID NO 19
<211> LENGTH: 21
<212> TYPE: DNA
<213> ORGANISM: Artificial Sequence
<220> FEATURE:
<223> OTHER INFORMATION: Synthetic DNA for a forward primer of At5g07580

<400> SEQUENCE: 19
atggcgagtt ttgaggaaag c         21

<210> SEQ ID NO 20
<211> LENGTH: 23
<212> TYPE: DNA
<213> ORGANISM: Artificial Sequence
<220> FEATURE:
<223> OTHER INFORMATION: Synthetic DNA for a reverse primer of At5g07580

<400> SEQUENCE: 20
aaatgcatca caggaagatg aag         23

<210> SEQ ID NO 21
<211> LENGTH: 22
<212> TYPE: DNA
<213> ORGANISM: Artificial Sequence
<220> FEATURE:
<223> OTHER INFORMATION: Synthetic DNA for a forward primer of At1g74930

<400> SEQUENCE: 21
atggtgaagc aagcgatgaa gg         22

<210> SEQ ID NO 22
<211> LENGTH: 24
<212> TYPE: DNA
<213> ORGANISM: Artificial Sequence
<220> FEATURE:
<223> OTHER INFORMATION: Synthetic DNA for a reverse primer of At1g74930

<400> SEQUENCE: 22
aaaatcccaa agaatcaaag attc         24

<210> SEQ ID NO 23
<211> LENGTH: 30
<212> TYPE: DNA

<213> ORGANISM: Artificial Sequence
<220> FEATURE:
<223> OTHER INFORMATION: Synthetic DNA for a forward primer of At5g47390

<400> SEQUENCE: 23
gatgactcgt cgatgttctc actgcaatca                                30

<210> SEQ ID NO 24
<211> LENGTH: 30
<212> TYPE: DNA
<213> ORGANISM: Artificial Sequence
<220> FEATURE:
<223> OTHER INFORMATION: Synthetic DNA for a reverse primer of At5g47390

<400> SEQUENCE: 24
taaagcgtgt atcacgcttt tgatgtctga                                30

<210> SEQ ID NO 25
<211> LENGTH: 21
<212> TYPE: DNA
<213> ORGANISM: Artificial Sequence
<220> FEATURE:
<223> OTHER INFORMATION: Synthetic DNA for a forward primer of At5g25190

<400> SEQUENCE: 25
atggcacgac cacaacaacg c                                         21

<210> SEQ ID NO 26
<211> LENGTH: 23
<212> TYPE: DNA
<213> ORGANISM: Artificial Sequence
<220> FEATURE:
<223> OTHER INFORMATION: Synthetic DNA for a reverse primer of At5g25190

<400> SEQUENCE: 26
cagcgtctga gttggtaaaa cag                                       23

<210> SEQ ID NO 27
<211> LENGTH: 30
<212> TYPE: DNA
<213> ORGANISM: Artificial Sequence
<220> FEATURE:
<223> OTHER INFORMATION: Synthetic DNA for a forward primer of At3g61910

<400> SEQUENCE: 27
gatgaacata tcagtaaacg gacagtcaca                                30

<210> SEQ ID NO 28
<211> LENGTH: 30
<212> TYPE: DNA
<213> ORGANISM: Artificial Sequence
<220> FEATURE:
<223> OTHER INFORMATION: Synthetic DNA for a reverse primer of At3g61910

<400> SEQUENCE: 28
tccactaccg ttcaacaagt ggcatgtcgt                                30

<210> SEQ ID NO 29
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(10)
<223> OTHER INFORMATION: Xaa is any amino acid

```
<220> FEATURE:
<221> NAME/KEY: misc_feature
<222> LOCATION: (14)..(14)
<223> OTHER INFORMATION: Xaa is Asn or Glu
<220> FEATURE:
<221> NAME/KEY: misc_feature
<222> LOCATION: (16)..(21)
<223> OTHER INFORMATION: Xaa is any amino acid

<400> SEQUENCE: 29

Xaa Xaa Xaa Xaa Xaa Xaa Xaa Xaa Xaa Xaa Leu Asp Leu Xaa Leu Xaa
1               5                   10                  15

Xaa Xaa Xaa Xaa Xaa
            20

<210> SEQ ID NO 30
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(10)
<223> OTHER INFORMATION: Xaa is any amino acid
<220> FEATURE:
<221> NAME/KEY: misc_feature
<222> LOCATION: (15)..(15)
<223> OTHER INFORMATION: Xaa is Phe or Ile
<220> FEATURE:
<221> NAME/KEY: misc_feature
<222> LOCATION: (16)..(21)
<223> OTHER INFORMATION: Xaa is any amino acid

<400> SEQUENCE: 30

Xaa Xaa Xaa Xaa Xaa Xaa Xaa Xaa Xaa Xaa Phe Asp Leu Asn Xaa Xaa
1               5                   10                  15

Xaa Xaa Xaa Xaa Xaa
            20

<210> SEQ ID NO 31
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: Xaa is Glu, Gln or Asp
<220> FEATURE:
<221> NAME/KEY: misc_feature
<222> LOCATION: (10)..(19)
<223> OTHER INFORMATION: Xaa is any amino acid

<400> SEQUENCE: 31

Leu Asp Leu Asp Leu Xaa Leu Arg Leu Xaa Xaa Xaa Xaa Xaa Xaa Xaa
1               5                   10                  15

Xaa Xaa Xaa

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa represents Glu, Gln, or Asp
```

```
<400> SEQUENCE: 32

Asp Leu Xaa Leu Arg Leu
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asp, Asn, Glu, Gln, Thr, or Ser
<220> FEATURE:
<221> NAME/KEY: misc_feature
<222> LOCATION: (3)..(3)
<223> OTHER INFORMATION: Xaa represents Asp, Gln, Asn, Arg, Glu, Thr,
      Ser, or His
<220> FEATURE:
<221> NAME/KEY: misc_feature
<222> LOCATION: (5)..(5)
<223> OTHER INFORMATION: Xaa represents Arg, Gln, Asn, Thr, Ser, His,
      Lys, or Asp

<400> SEQUENCE: 33

Xaa Leu Xaa Leu Xaa Leu
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asp, Asn, Glu, Gln, Thr, or Ser
<220> FEATURE:
<221> NAME/KEY: misc_feature
<222> LOCATION: (3)..(3)
<223> OTHER INFORMATION: Xaa represents Asp, Gln, Asn, Arg, Glu, Thr,
      Ser, or His
<220> FEATURE:
<221> NAME/KEY: misc_feature
<222> LOCATION: (5)..(5)
<223> OTHER INFORMATION: Xaa represents Gln, Asn, Thr, Ser, His, Lys,
      or Asp

<400> SEQUENCE: 34

Xaa Leu Xaa Leu Xaa Leu
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asp, Asn, Glu, Gln, Thr, or Ser
<220> FEATURE:
<221> NAME/KEY: misc_feature
<222> LOCATION: (3)..(3)
<223> OTHER INFORMATION: Xaa represents Asn, Arg, Thr, Ser, or His

<400> SEQUENCE: 35

Xaa Leu Xaa Leu Arg Leu
```

```
<210> SEQ ID NO 36
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa represents Asn, Glu, Gln, Thr, or Ser
<220> FEATURE:
<221> NAME/KEY: misc_feature
<222> LOCATION: (3)..(3)
<223> OTHER INFORMATION: Xaa represents Asp, Gln, Asn, Arg, Glu, Thr,
      Ser, or His

<400> SEQUENCE: 36

Xaa Leu Xaa Leu Arg Leu
1               5

<210> SEQ ID NO 37
<211> LENGTH: 13
<212> TYPE: PRT
<213> ORGANISM: Artificial Sequence
<220> FEATURE:
<223> OTHER INFORMATION: Synthetic peptide

<400> SEQUENCE: 37

Gly Leu Asp Leu Asp Leu Glu Leu Arg Leu Gly Phe Ala
1               5                   10
```